(12) United States Patent
Bock et al.

(10) Patent No.: US 6,878,813 B2
(45) Date of Patent: Apr. 12, 2005

(54) HUMAN ANTITHROMBIN IIIS AND METHODS RELATED THERETO

(75) Inventors: Susan C. Bock, Salt Lake City, UT (US); Veronique Picard, Bourg la Reine (FR); Pedram Zendehrouh, Hamden, CT (US)

(73) Assignees: Temple University - of the Commonwealth System of Higher Education, Philadelphia, PA (US); University of Utah Research Foundation, Salt Lake City, UT (US)

( * ) Notice: Subject to any disclaimer, the term of this patent is extended or adjusted under 35 U.S.C. 154(b) by 386 days.

(21) Appl. No.: 10/014,658

(22) Filed: Dec. 11, 2001

(65) Prior Publication Data

US 2005/0032681 A1 Feb. 10, 2005

Related U.S. Application Data

(63) Continuation of application No. 09/305,588, filed on May 5, 1999.
(60) Provisional application No. 60/085,197, filed on May 12, 1998.

(51) Int. Cl.[7] ........................ A61K 35/14; C07K 14/00
(52) U.S. Cl. .................... 530/393; 530/350; 530/380; 530/381; 530/395; 930/10; 930/250
(58) Field of Search ............................... 530/350, 380, 530/381, 393, 395; 930/10, 250

(56) References Cited

U.S. PATENT DOCUMENTS

| | | | |
|---|---|---|---|
| 5,204,253 A | 4/1993 | Sanford et al. .......... | 435/172.3 |
| 5,420,252 A | 5/1995 | Kato et al. .................. | 530/393 |
| 5,618,713 A | 4/1997 | Zettlmeissl .................. | 435/226 |
| 5,700,663 A | 12/1997 | Zettlmeissl et al. ........ | 435/69.6 |
| 5,843,705 A | 12/1998 | DiTullio et al. ........... | 435/69.1 |

FOREIGN PATENT DOCUMENTS

| | | |
|---|---|---|
| EP | 0 568 833 A1 | 8/1993 |
| WO | WO 91/00291 | 1/1991 |
| WO | WO 95/05853 | 3/1995 |
| WO | WO 95/19799 | 7/1995 |

OTHER PUBLICATIONS

Cunningham et al. Development of an Elastase–Resistant antithrombin through mutagenesis at P4. (1995) Blood 86(10) SUPP p. 357A.*

Cunningham et al. Development of an Elastase–Resistant antithrombin through mutagenesis at P4. (1995) Blood 86(10) SUPPL. p. 357A.*

Blauhut et al. "Substitution of antithrombin III in shock and DIC: a randomized study." Thromb Res. Jul. 1, 1985;39(1):81–9.

Buller and ten Cate, "Acquired antithrombin III deficiency: laboratory diagnosis, incidence, clinical implications, and treatment with antithrombin III concentrate." Am J Med. Sep. 11, 1989;87(3B):44S–48S.

Damus and Wallace, "Immunologic measurement of antithrombin III–heparin cofactor and $\alpha_2$–macroglobulin in disseminated intravascular coagulation and hepatic failure coagulopathy." Thromb Res. Jan. 1975;6(1):27–38.

Delshammar et al. "Abnormal proteolysis (DIC)—successful treatment with antithrombin III concentrate and a concentrate containing F XIII and native von Willebrand factor." J Intern Med. Jan. 1989;225(1):21–7.

Dickneite and Paques, "Reduction of mortality with antithrombin III in septicemic rats: a study of Klebsiella pneumoniae induced sepsis." Thromb Haemost. Feb. 1, 1993;69(2):98–100, 102.

Emerson et al. "Efficacy of antithrombin III supplementation in animal models of fulminant *Escherichia coli* endotoxemia or bacteremia." Am. J. Med. Sep. 11, 1989;87(3B):27S–33S.

Ersdal–Badju et al. Elimination of glycosylation heterogeneity affecting heparin affinity of recombinant human antithrombin III by expression of a β–like variant in baculovirus–infected insect cells. Biochem. J. Aug. 15, 1995;310:323–30.

Fourrier et al. "Double–blind, placebo–controlled trial of antithrombin III concentrates in septic shock with disseminated intravascular coagulation." Chest. Sep. 1993;104(3)882–8.

Franzen et al. "Structural Studies on the Carbohydrate Portion of Human Antithrombin III." J. Biol. Chem. Jun. 10, 1980;255(11):5090–3.

Hedin et al. "Antithrombin III inhibits thrombin–induced proliferation in human arterial smooth muscle cells." Arterioscler Thromb. Feb. 1994;14(2):254–60.

Hellgren et al. "Blood coagulation and fibrinolytic factors and their inhibitors in critically ill patients." Intensive Care Med. 1984;10(1):23–8.

Hellgren et al. "Antithrombin III concentrate as adjuvant in DIC treatment. A pilot study in 9 severely ill patients." Thromb Res. Aug. 15, 1984;35(4):459–66.

Jochum, "Influence of high–dose antithrombin concentrate therapy on the release of cellular proteinases, cytokines, and soluble adhesion molecules in acute inflammation." Semin Hematol. Oct. 1995;32(4 Suppl 2):19–32.

(Continued)

*Primary Examiner*—Jon Weber
*Assistant Examiner*—Holly Schnizer
(74) *Attorney, Agent, or Firm*—Needle & Rosenberg, P.C.

(57) ABSTRACT

The present invention discloses modified antithrombin III compounds and methods. The amino acid compounds of the present invention are useful in treating blood clotting disorders, as well as other disease states associated with enzymes in the coagulation pathway.

138 Claims, No Drawings

OTHER PUBLICATIONS

Kurachi et al. "Inhibition of Bovine Factor $IX_a$ and Factor $X_{a\beta}$ by Antithrombin III." Biochemistry Jan. 27, 1976;15(2):373–7.

Lammle et al. "Plasma prekallikrein, factor XII, antithrombin III, $C_1$–inhibitor and $\alpha_2$–macroglobulin in critically ill patients with suspected disseminated intravascular coagulation (DIC)." Am J Clin Pathol. Oct. 1984;82(4):396–404.

Lawson et al. "Complex–dependent inhibition of factor VIIa by antithrombin III and heparin." J. Biol. Chem. Jan. 15, 1993: 268(2):767–70.

Mammen et al. "Human antithrombin concentrates and experimental disseminated intravascular coagulation." Semin Thromb Hemost. Oct. 1985;11(4):373–83.

Mant et al. "Haemorrhagic complications of heparin therapy." Lancet. May 28, 1977;1(8022):1133–5.

Marcum et al. "Microvascular heparinlike species with anticoagulant activity." Am. J. Physiol. Nov. 1983;245(5 Pt 1):H725–33.

Mizuochi et al. "Structural studies of the carbohydrate moiety of human antithrombin III." Arch Biochem Biophys. Aug. 1980;203(1):458–65.

Nuijens et al. "Plasma elastase $\alpha_1$–antitrypsin and lactoferrin in sepsis: evidence for neutrophils as mediators in fatal sepsis." J Lab Clin Med. Feb. 1992;119(2):159–68.

Ostrovsky et al. "Antithrombin III prevents and rapidly reverses leukocyte recruitment in ischemia/reperfusion." Circulation. Oct. 1997;96(7):2302–10.

Petersen et al. *The Physiological Inhibitors of Coagulation and Fibrinolysis*. 43–54. Elsevier/North Holland Biomedical Press (1979).

Peterson and Blackburn, "Isolation and characterization of an antithrombin III variant with reduced carbohydrate content and enhanced heparin binding." J. Biol. Chem. Jan. 10, 1985;260(1):610–5.

Picard and Bock, *Methods in Molecular Biology*, vol. 67: *PCR Cloning Protocols: From Molecular Cloning to Genetic Engineering*. 183–8. B. A. White Humana Press Inc., Totowa, NJ (1996).

Picard et al. "A rapid and efficient one–tube PCR–based mutagenesis technique using *Pfu* DNA polymerase." Nucleic Acids Res. Jul. 11, 1994;22(13):2587–91.

Rao et al. "Binding of factor VIIa to tissue factor permits rapid antithrombin III/heparin inhibition of factor VIIa." Blood. May 15, 1993;81(10):2600–7.

Rosenberg and Damus, "The purification and mechanism of action of human antithrombin–heparin cofactor." J. Biol. Chem. Sep. 25, 1973;248(18):6490–505.

Rosenberg, "Chemistry of the hemostatic mechanism and its relationship to the action of heparin." Fed Proc. Jan. 1977;36(1):10–8.

Ruf and Mueller,"Tissue factor in cancer angiogenesis and metastasis." Curr Opin Hematol. Sep. 1996;3(5):379–84.

Seitz et al. "Participation and interactions of neutrophil elastase in haemostatic disorders of patients with severe infections." Eur J Haematol. Mar. 1987;38(3):231–40.

Uchiba and Okajima, "Antithrombin III (AT III) prevents LPS–induced pulmonary vascular injury: novel biological activity of AT III." Semin Thromb Hemost. 1997;23(6):583–90.

Van Boven and Lane, "Antithrombin and its inherited deficiency states." Semin Hematol. Jul. 1997;34(3):188–204.

Wolff et al. "Direct gene transfer into mouse muscle in vivo." Science Mar. 23, 1990;247(4949 PT 1):1465–8.

Zendehrouh, "Novel proteinase inhibitors for use in the treatment of sepsis." *Dissertation submitted to the Temple University Graduate Board*, 165 pages (May 1998).

Bock et al, *10 Nucleic Acids Res.* 8113 (1982) .

Jochum et al, *362 Hoppe–Seyler's Z. Physiol. Chem.* 103 (1981).

Carrell and Owen, *317 Nature* 730 (1985).

Jordan et al, *237 Science* 777 (1987).

Bick et al, *73 Am. J. Clin. Path.* 577 (1980).

Vinazzer, *1 Clin. Appl. Thrombosis/Hemostasis* 62 (1995).

Brennan et al., *219 FEBS Lett.* 431 (1987).

Picard et al, *34 Biochemistry* 8433 (1995).

Cunningham et al, *88 Thrombsis Res* 171 (1997).

69th Scientific Sessions. Abstract No. 4336, Kato et al. 'Recombinant Antithrombin III Mutants with Enhanced Antithrombin Activity without Heparin.' 1996, vol. 94, No. 8 suppl., p. I–741.

Stephens, et al. Site–directed Mutagenesis of the Reactive Center (Serine 394) of Antithrombin III. J. Biol. Chem. Nov. 5, 1988, vol. 263, No. 31, pp. 15849–15852.

Owen et al. "P1 variant antithrombins Glasgow (393 Arg to His) and Pescara (393 Arg to Pro) have increased heparin affinity and are resistant to catalytic cleavage by elastase" 380(2)216–220, Mar. 1991.

* cited by examiner

SEQUENCE LISTING

<160> NUMBER OF SEQ ID NOS: 35

<210> SEQ ID NO 1
<211> LENGTH: 9
<212> TYPE: PRT
<213> ORGANISM: Homo sapiens

<400> SEQUENCE: 1

Ser Thr Ala Leu Glu Ala Ile Gly Arg
1               5

<210> SEQ ID NO 2
<211> LENGTH: 9
<212> TYPE: PRT
<213> ORGANISM: Homo sapiens

<400> SEQUENCE: 2

Ser Thr Glu Val Glu Ala Ala Gly Arg
1               5

<210> SEQ ID NO 3
<211> LENGTH: 9
<212> TYPE: PRT
<213> ORGANISM: Homo sapiens

<400> SEQUENCE: 3

Ser Thr Ala Val Glu Ala Ala Gly Arg
1               5

<210> SEQ ID NO 4
<211> LENGTH: 9
<212> TYPE: PRT
<213> ORGANISM: Homo sapiens

<400> SEQUENCE: 4

Ser Thr Glu Gly Phe Phe Ser Gly Arg
1               5

<210> SEQ ID NO 5
<211> LENGTH: 9
<212> TYPE: PRT
<213> ORGANISM: Homo sapiens

<400> SEQUENCE: 5

Ser Thr Glu Gly Glu Ala Ser Gly Arg
1               5

<210> SEQ ID NO 6
<211> LENGTH: 9
<212> TYPE: PRT
<213> ORGANISM: Homo sapiens

<400> SEQUENCE: 6

Ser Thr Glu Gly Glu Gly Ser Gly Arg
1               5

<210> SEQ ID NO 7
<211> LENGTH: 9
<212> TYPE: PRT
<213> ORGANISM: Homo sapiens

<400> SEQUENCE: 7

Ser Glu Glu Gly Glu Ala Ser Gly Arg

```
                1               5

<210> SEQ ID NO 8
<211> LENGTH: 9
<212> TYPE: PRT
<213> ORGANISM: Homo sapiens

<400> SEQUENCE: 8

Ser Glu Glu Gly Glu Gly Ser Gly Arg
1               5

<210> SEQ ID NO 9
<211> LENGTH: 9
<212> TYPE: PRT
<213> ORGANISM: Homo sapiens

<400> SEQUENCE: 9

Ser Thr Ala Val Glu Gly Ala Gly Arg
1               5

<210> SEQ ID NO 10
<211> LENGTH: 9
<212> TYPE: PRT
<213> ORGANISM: Homo sapiens

<400> SEQUENCE: 10

Ser Thr Glu Val Glu Gly Ala Gly Arg
1               5

<210> SEQ ID NO 11
<211> LENGTH: 9
<212> TYPE: PRT
<213> ORGANISM: Homo sapiens

<400> SEQUENCE: 11

Ser Thr Glu Leu Glu Gly Ala Gly Arg
1               5

<210> SEQ ID NO 12
<211> LENGTH: 9
<212> TYPE: PRT
<213> ORGANISM: Homo sapiens

<400> SEQUENCE: 12

Ser Thr Ala Leu Glu Gly Ala Gly Arg
1               5

<210> SEQ ID NO 13
<211> LENGTH: 9
<212> TYPE: PRT
<213> ORGANISM: Homo sapiens

<400> SEQUENCE: 13

Ser Thr Ala Glu Gly Gly Gly Gly Arg
1               5

<210> SEQ ID NO 14
<211> LENGTH: 9
<212> TYPE: PRT
<213> ORGANISM: Homo sapiens

<400> SEQUENCE: 14

Ser Thr Gln Thr Pro Pro Asn Gly Arg
1               5
```

<210> SEQ ID NO 15
<211> LENGTH: 9
<212> TYPE: PRT
<213> ORGANISM: Homo sapiens

<400> SEQUENCE: 15

Ser Thr Ala Val Phe Phe Ala Gly Arg
 1               5

<210> SEQ ID NO 16
<211> LENGTH: 1525
<212> TYPE: DNA
<213> ORGANISM: Homo sapiens

<400> SEQUENCE: 16

| | | | | | |
|---|---|---|---|---|---|
| gatcacacta | tctccacttg | cccagccctg | tggaagatta | gcggccatgt | attccaatgt | 60 |
| gataggaact | gtaacctctg | aaaaaggaa | ggtttatctt | ttgtccttgc | tgctcattgg | 120 |
| cttctgggac | tgcgtgacct | gtcacgggag | ccctgtggac | atctgcacag | ccaagccgcg | 180 |
| ggacattccc | atgaatccca | tgtgcattta | ccgctcccg | gagaagaagg | caactgagga | 240 |
| tgagggctca | gaacagaaga | tcccggaggc | caccaaccgg | cgtgtctggg | aactgtccaa | 300 |
| ggccaattcc | cgctttgcta | ccactttcta | tcagcacctg | gcagattcca | agaatgacaa | 360 |
| tgataacatt | ttcctgtcac | ccctgagtat | ctccacggct | tttgctatga | ccaagctggg | 420 |
| tgcctgtaat | gacaccctcc | agcaactgat | ggaggtattt | aagtttgaca | ccatatctga | 480 |
| gaaaacatct | gatcagatcc | acttcttctt | tgccaaactg | aactgccgac | tctatcgaaa | 540 |
| agccaacaaa | tcctccaagt | tagtatcagc | caatcgcctt | tttggagaca | aatcccttac | 600 |
| cttcaatgag | acctaccagg | acatcagtga | gttggtatat | ggagccaagc | tccagcccct | 660 |
| ggacttcaag | gaaaatgcag | agcaatccag | agcggccatc | aacaaatggg | tgtccaataa | 720 |
| gaccgaaggc | cgaatcaccg | atgtcattcc | ctcggaagcc | atcaatgagc | tcactgttct | 780 |
| ggtgctggtt | aacaccattt | acttcaaggg | cctgtggaag | tcaaagttca | gccctgagaa | 840 |
| cacaaggaag | gaactgttct | acaaggctga | tggagagtcg | tgttcagcat | ctatgatgta | 900 |
| ccaggaaggc | aagttccgtt | atcggcgcgt | ggctgaaggc | acccaggtgc | ttgagttgcc | 960 |
| cttcaaaggt | gatgacatca | ccatggtcct | catcttgccc | aagcctgaga | gagcctggc | 1020 |
| caaggtggag | aaggaactca | ccccagaggt | gctgcaggag | tggctggatg | aattggagga | 1080 |
| gatgatgctg | gtggttcaca | tgccccgctt | ccgcattgag | gacggcttca | gtttgaagga | 1140 |
| gcagctgcaa | gacatgggcc | ttgtcgatct | gttcagccct | gaaaagtcca | actcccagg | 1200 |
| tattgttgca | gaaggccgag | atgacctcta | tgtctcagat | gcattccata | aggcatttct | 1260 |
| tgaggtaaat | gaagaaggca | gtgaagcagc | tgcaagtacc | gctgttgtga | ttgctggccg | 1320 |
| ttcgctaaac | cccaacaggg | tgactttcaa | ggccaacagg | cccttcctgg | tttttataag | 1380 |
| agaagttcct | ctgaacacta | ttatcttcat | gggcagagta | gccaaccctt | gtgttaagta | 1440 |
| aaatgttctt | attctttgca | cctcttccta | tttttggttt | gtgaacagaa | gtaaaaataa | 1500 |
| atacaaacta | cttccatctc | acatt | | | | 1525 |

<210> SEQ ID NO 17
<211> LENGTH: 36
<212> TYPE: DNA
<213> ORGANISM: Homo sapiens

<400> SEQUENCE: 17
accgcggaag gaggaggcgg ccgttcgcta aacccc        36

<210> SEQ ID NO 18
<211> LENGTH: 29
<212> TYPE: DNA
<213> ORGANISM: Homo sapiens

<400> SEQUENCE: 18
accgctgttt tcttcgccgg ccgttcgct        29

<210> SEQ ID NO 19
<211> LENGTH: 48
<212> TYPE: DNA
<213> ORGANISM: Homo sapiens

<400> SEQUENCE: 19
accgaaggtt tcttctctgg ccgttctta aaccccaaca gggtgact        48

<210> SEQ ID NO 20
<211> LENGTH: 48
<212> TYPE: DNA
<213> ORGANISM: Homo sapiens

<400> SEQUENCE: 20
acccaaactt tcttcaacgg ccgaagctta aaccccaaca gggtgact        48

<210> SEQ ID NO 21
<211> LENGTH: 34
<212> TYPE: DNA
<213> ORGANISM: Homo sapiens

<400> SEQUENCE: 21
ctgcaagtac tgaaggtgaa gcttctggcc gttc        34

<210> SEQ ID NO 22
<211> LENGTH: 34
<212> TYPE: DNA
<213> ORGANISM: Homo sapiens

<400> SEQUENCE: 22
ctgcaagtac tgaaggtgaa ggttctggcc gttc        34

<210> SEQ ID NO 23
<211> LENGTH: 40
<212> TYPE: DNA
<213> ORGANISM: Homo sapiens

<400> SEQUENCE: 23
aagcagctgc tagcgaagaa ggtgaagctt ctggccgttc        40

<210> SEQ ID NO 24
<211> LENGTH: 40
<212> TYPE: DNA
<213> ORGANISM: Homo sapiens

<400> SEQUENCE: 24
aagcagctgc tagcgaagaa ggtgaaggtt ctggccgttc        40

<210> SEQ ID NO 25
<211> LENGTH: 32
<212> TYPE: DNA
<213> ORGANISM: Homo sapiens

<400> SEQUENCE: 25
ctgcaagtac tgctgttgaa ggtgctggcc gt                32

<210> SEQ ID NO 26
<211> LENGTH: 32
<212> TYPE: DNA
<213> ORGANISM: Homo sapiens

<400> SEQUENCE: 26
ctgcaagtac tgaggttgaa ggtgctggcc gt                32

<210> SEQ ID NO 27
<211> LENGTH: 32
<212> TYPE: DNA
<213> ORGANISM: Homo sapiens

<400> SEQUENCE: 27
ctgcaagtac tgagcttgaa ggtgctggcc gt                32

<210> SEQ ID NO 28
<211> LENGTH: 32
<212> TYPE: DNA
<213> ORGANISM: Homo sapiens

<400> SEQUENCE: 28
ctgcaagtac tgctcttgaa ggtgctggcc gt                32

<210> SEQ ID NO 29
<211> LENGTH: 32
<212> TYPE: DNA
<213> ORGANISM: Homo sapiens

<400> SEQUENCE: 29
ctgcaagtac tgctgttgag gctgctggcc gt                32

<210> SEQ ID NO 30
<211> LENGTH: 32
<212> TYPE: DNA
<213> ORGANISM: Homo sapiens

<400> SEQUENCE: 30
ctgcaagtac tgaggttgag gctgctggcc gt                32

<210> SEQ ID NO 31
<211> LENGTH: 18
<212> TYPE: DNA
<213> ORGANISM: Homo sapiens

<400> SEQUENCE: 31
tattgttgca gaaggccg                                18

<210> SEQ ID NO 32
<211> LENGTH: 16
<212> TYPE: DNA
<213> ORGANISM: Homo sapiens

<400> SEQUENCE: 32
aacagctatg accatg                                  16

<210> SEQ ID NO 33
<211> LENGTH: 24
<212> TYPE: DNA
<213> ORGANISM: Homo sapiens -continued

```
<400> SEQUENCE: 33
agcggataac aatttcacac agga                                    24

<210> SEQ ID NO 34
<211> LENGTH: 36
<212> TYPE: DNA
<213> ORGANISM: Homo sapiens

<400> SEQUENCE: 34
tagcgaacgg ccgatagcct caagagcggt acttgc                       36

<210> SEQ ID NO 35
<211> LENGTH: 432
<212> TYPE: PRT
<213> ORGANISM: Artificial Sequence
<220> FEATURE:
<223> OTHER INFORMATION: Description of Artificial Sequence:/note =
      synthetic construct

<400> SEQUENCE: 35
```

His Gly Ser Pro Val Asp Ile Cys Thr Ala Lys Pro Arg Asp Ile Pro
1               5                   10                  15

Met Asn Pro Met Cys Ile Tyr Arg Ser Pro Glu Lys Lys Ala Thr Glu
                20                  25                  30

Asp Glu Gly Ser Glu Gln Lys Ile Pro Glu Ala Thr Asn Arg Arg Val
            35                  40                  45

Trp Glu Leu Ser Lys Ala Asn Ser Arg Phe Ala Thr Thr Phe Tyr Gln
        50                  55                  60

His Leu Ala Asp Ser Lys Asn Asp Asn Asp Asn Ile Phe Leu Ser Pro
65                  70                  75                  80

Leu Ser Ile Ser Thr Ala Phe Ala Met Thr Lys Leu Gly Ala Cys Asn
                85                  90                  95

Asp Thr Leu Gln Gln Leu Met Glu Val Phe Lys Phe Asp Thr Ile Ser
            100                 105                 110

Glu Lys Thr Ser Asp Gln Ile His Phe Phe Phe Ala Lys Leu Asn Cys
        115                 120                 125

Arg Leu Tyr Arg Lys Ala Asn Lys Ser Ser Lys Leu Val Ser Ala Asn
    130                 135                 140

Arg Leu Phe Gly Asp Lys Ser Leu Thr Phe Asn Glu Thr Tyr Gln Asp
145                 150                 155                 160

Ile Ser Glu Leu Val Tyr Gly Ala Lys Leu Gln Pro Leu Asp Phe Lys
                165                 170                 175

Glu Asn Ala Glu Gln Ser Arg Ala Ala Ile Asn Lys Trp Val Ser Asn
            180                 185                 190

Lys Thr Glu Gly Arg Ile Thr Asp Val Ile Pro Ser Glu Ala Ile Asn
        195                 200                 205

Glu Leu Thr Val Leu Val Leu Val Asn Thr Ile Tyr Phe Lys Gly Leu
    210                 215                 220

Trp Lys Ser Lys Phe Ser Pro Glu Asn Thr Arg Lys Glu Leu Phe Tyr
225                 230                 235                 240

Lys Ala Asp Gly Glu Ser Cys Ser Ala Ser Met Met Tyr Gln Glu Gly
                245                 250                 255

Lys Phe Arg Tyr Arg Arg Val Ala Glu Gly Thr Gln Val Leu Glu Leu
            260                 265                 270

Pro Phe Lys Gly Asp Asp Ile Thr Met Val Leu Ile Leu Pro Lys Pro
        275                 280                 285

```
                            -continued
Glu Lys Ser Leu Ala Lys Val Glu Lys Glu Leu Thr Pro Glu Val Leu
    290                 295             300

Gln Glu Trp Leu Asp Glu Leu Glu Glu Met Met Leu Val Val His Met
305             310             315                         320

Pro Arg Phe Arg Ile Glu Asp Gly Phe Ser Leu Lys Glu Gln Leu Gln
                325             330                 335

Asp Met Gly Leu Val Asp Leu Phe Ser Pro Glu Lys Ser Lys Leu Pro
            340             345             350

Gly Ile Val Ala Glu Gly Arg Asp Asp Leu Tyr Val Ser Asp Ala Phe
        355             360                 365

His Lys Ala Phe Leu Glu Val Asn Glu Glu Gly Ser Glu Ala Ala Ala
    370             375             380

Ser Thr Ala Val Val Ile Ala Gly Arg Ser Leu Asn Pro Asn Arg Val
385             390             395                     400

Thr Phe Lys Ala Asn Arg Pro Phe Leu Val Phe Ile Arg Glu Val Pro
            405             410             415

Leu Asn Thr Ile Ile Phe Met Gly Arg Val Ala Asn Pro Cys Val Lys
            420             425             430
```

HUMAN ANTITHROMBIN IIIS AND METHODS RELATED THERETO

This application is a continuation application of and claims priority to U.S. patent application Ser. No. 09/305,588, filed May 5, 1999, which claims priority to U.S. Provisional Patent Application Ser. No. 60/085,197, filed May 12, 1998, both of which are hereby incorporated by this reference in their entirety.

The present invention was supported in part by a grant from the National Institutes of Health, Grant Number HL-56914; the U.S. Government may have certain rights in this invention.

FIELD OF THE INVENTION

The present invention relates to the field of antithrombins, and materials and methods useful to alter natural processes affected by antithrombins. For instance, the present invention provides human antithrombin IIIs (ATIIIs) which: have surprising resistance to elastase inactivation; have resistance to inactivation by IgG-activated neutrophils; retain antithrombin activity; and/or retain or have surprising antifactor Xa activity. These ATIIIs may be expressed as glycoforms with enhanced heparin affinity which target the blood vessel wall more efficiently than ATIIIs with normal heparin affinity. The present invention the re fore relates broadly to recombinant DNA technology, molecular biology tools, and disease treatments.

BACKGROUND OF THE INVENTION

ATIII is a major inhibitor of enzymes in the coagulation cascade, including thrombin (Rosenberg and Damus, (1973) *J. Biol. Chem.*, 248, 6490–6505) and factor Xa (Kurachi et al., (1976) *Biochemistry*, 15, 373–377). Many hereditary mutations in ATIII have been identified that promote hypercoagulability because of unchecked activity of the coagulation enzymes (Reviewed in van Boven and Lane, (1997) *Semin. Hematol.*, 34, 188–204). Acquired deficiencies of ATIII can also occur with negative repercussions on hemostasis, as for example during septic disseminated intravascular coagulopathy (DIC) (Bick et al., (1980) *Am. J. Clin. Path.*, 73, 577–583); (Buller and Cate, (1989) *Am. J. Med.*, 87, 44S–48S); (Damus and Wallace, (1989) *Thromb. Res.*, 6, 27); (Hellgren et al., (1984) *Intensive Care Med.*, 10, 23–28); (Lammle et al., (1984) *Am J Clin Pathol*, 82, 396–404); (Mammen et al., (1985) *Semin. Thromb. Hemost.*, 11, 373–383). In contrast, hemorrhage resulting from excess inhibition of blood coagulation by ATIII can occur in the presence of pharmaceutical heparin, which is frequently used to treat and prevent hypercoagulable states Giant et al., (1977) *Lancet*, 1, 1133–1135).

ATIII is a 432 amino acid Mr 58 000 plasma glycoprotein (Bock et al., (1982) *Nucleic Acids Res.*, 10, 8113–8125); (Petersen et al., (1979) *The Physiological Inhibitors of Coagulation and Fibrinolysis* (pp. 43–54): Elsevier/North Holland Biomedical Press) which not only inhibits thrombin and factor Xa, but also serine proteinases preceding them in the intrinsic pathway (e.g., factor IXa, factor XIa, factor XIIa) (Rosenberg, (1977) *Fed. Proc.*, 36, 10–18) and the extrinsic pathway (factor VIIa-TF) (Lawson et al., (1993) *J. Biol. Chem.*, 268: 767–770); (Rao et al., (1993) *Blood*, 81: 2600–2607) of blood coagulation. Factor VIIa-TF has roles not only in coagulation and thrombosis, but is implicated in cancer angiogenesis and metastasis as well (Ruf and Mueller, (1996) *Curr. Opin. Hematol.*, 3: 379–84). ATIII also effects non-coagulant, thrombin-mediated pathways, such as thrombin-induced smooth muscle cell proliferation (Hedin et al., (1994) *Arterioscler. Thromb.*, 14: 254–260) and thrombin-mediated neutrophil extravasation (Ostrovsky et al., (1997) *Circulation*, 96: 2302–2310). Moreover, ATIII promotes endothelial release of prostacyclin (PGI2), which inhibits leukocyte and platelet activation, and has vasodialator properties (Uchiba et al., (1997) *Seminars in Thrombosis and Hemostasis*, 23: 583–590).

The inhibitory activity of ATIII towards its target enzymes is dramatically enhanced by heparin (Rosenberg and Damus, (1973) *J. Biol. Chem.*, 248, 6490–6505) and vascular surface heparan sulfate proteoglycans (HSPGs) (Marcum et al., (1983) *Am. J. Physiol.*, 245: H725–733) The, heparin binding property of antithrombin directs ATIII to sites where its target enzymes are generated, and potentiates its activity on these surfaces.

Antithrombin is synthesized in the liver and secreted in the blood as two different isoforms (Peterson and Blackburn, (1985) *J. Biol. Chem.*, 260, 610–615). The predominant species (90%), α-ATIII, has four identical N-glycosidic-linked polysaccharide chains attached to asparagine residues 96, 135, 155, and 192 (Franzen et at., (1980) *J. Biol. Chem.*, 255, 5090–5093); (Mizuochi et al., (1980) *Arch. Biochem. Biophys.*, 203, 458–465). The minor β-ATIII isoform (10%) lacks the oligosaccharide side chain at asparagine 135 (Brennan et al., (1987) *FEBS Lett.*, 219, 431–436). The β-glycoform lacks a carbohydrate on Asn-135 because of inefficient glycosylation of the NXS consensus sequence (Picard et al., (1995) *Biochemistry*, 34, 8433–8440). U.S. Pat. Nos. 5,618,713 and 5,7000,663 disclose that mutation at one or more glycosylation sites (for example Asn 135, Asn 155) increases the heparin-binding/heparin-activating properties while retaining the protease specificity of ATM. In particular, those patents disclose and claim modified ATIIIs with replacement of asparagines in N-glycosylation sites by residues which are incapable of being glycosylated. U.S. Pat. Nos. 5,618,713 and 5,700,663 do not disclose the present ATIIIs with improved resistance to human neutrophil elastase or enhanced heparin affinity due to mutation of the third position in N-glycosylation sequences.

Human neutrophil elastase cleaves and inactivates ATIII (Jochum et al., (1981). *Hoppe-Seyler's Z. Physiol. Chem.*, 362, 103–112). The reported neutrophil elastase cleavage sites were after the P5-Val and P4-Ile (Carrell and Owen, (1985) *Nature*, 317, 730–732). Furthermore, Jordan and colleagues showed that elastase inactivation of ATIII was heparin dependent (Jordan et al., (1987) *Science*, 237, 777–779). It has been hypothesized that elevated elastase (Nuijens et al., (1992) *J. Lab. Clin. Med.*, 119, 159–168) is responsible for the inactivation of ATIII in sepsis (Seitz et al., (1987) *Eur. J. Haematol.*, 38, 231–240) and reduced antithrombin levels in septic DIC (Bick et al., (1980) *Am. J. Clin. Path.*, 73, 577–583); (Buller and ten Cate, (1989) *Am. J. Med.*, 87, 44S–48S); (Damus and Wallace, (1989) *Thromb. Res.*, 6, 27); (Hellgren et al., (1984a) *Intensive Care Med.*, 10, 23–28); (Lammle et al., (1984) *Am J Clin Pathol*, 82, 396–404); (Mammen et al., (1985) *Semin. Thromb. Hemost.*, 11, 373–383). This acquired decrease in functional ATIII would contribute to the progression of DIC due to the inability to inhibit activated coagulation proteinases, ultimately leading to thrombin activation, fibrin formation and coagulation factor consumption.

Several animal and human studies have suggested that ATIII concentrate therapy may be effective in reducing mortality rates of patients suffering from septic disseminated intravascular coagulopathy (DIC). Using an endotoxemic rat model, (Emerson et al. (1987) *Am. J. Med.*, 87, 27S–33S)

have shown that prophylactic ATIII treatment affords protection from the decline of hemostasis associated with septicemia complicated by DIC. ATIII treatment has also been found to be effective in reducing mortality and stabilizing hemostatic parameters when administered after the presence of DIC has been established in *Klebsiella pneumoniae*—induced septicemic rats (Dickneite and Paques, (1993) *Thromb. Haemost.*, 69, 98–102). Human studies of ATIII replacement therapy have also shown promising results. Patients with septic shock and DIC showed improved survival as well as improved hematologic characteristics and organ function parameters with ATIII substitution (Blauhut et al., (1985) *Thromb. Res.*, 39, 81–89); (Delshammar et al., (1989). *J. Intern. Med.*, 225, 21–27); (Fourrier et al., (1993) *Chest*, 104, 882–888); (Hellgren et al., (1984b) *Thromb. Res.*, 35, 459–466); (Jochum, (1995) *Semin. Hematol.*, 32, 19–32). Review of the various patient trials showed a survival rate ranging from 64–97% (combined, 76%) among those receiving ATIII replacement, compared to a survival range of 7.6–25% (combined, 19%) (Vinazzer, (1995) *Clin. Appl. Thrombosis/Hemostasis*, 1,62–65). These studies showed promising responses to ATIII concentrates in the treatment of septic DIC. However, very large doses of ATIII were required (90–120 U/kg/day) (Fourrier et al., (1993) *Chest.* 104, 882–888); (Jochum, (1995) *Semin. Hematol.*, 32, 19–32). This finding was consistent with continued inactivation of the exogenous ATIII by elevated levels of neutrophil elastase. These observations suggested that reversal of septic DIC may be achievable using lower doses of recombinant ATIII variants with engineered resistance to the neutrophil proteinases elastase, cathepsin G and proteinase-3.

Previous attempts at replacing the elastase cleavage site with non-cleavable residues has resulted in impaired thrombin binding inhibition. The authors "report that the reiteration of the substitution best fitting these criteria, that of Trp at both P4 and P5 [residues 389 and 390], does not confer significant LE [neutrophil elastase] resistance on AT." Cunningham et al, 88 Thrombsis Res 171 (1997). These modified ATIIIs were considered commercially available compared to wild-type ATIII.

WO 91/00291 also discloses modified antithrombin III variants. It broadly describes modified ATIIIs wherein "at least one amino acid from the region comprising amino acids 384–396 is replaced by the corresponding amino acids group around the factor Xa cleavage site in factor II related to the formation of meizothrombin . . . " The present ATIIIs were not mentioned in that publication.

Citation of the above documents is not intended as an admission that any of the foregoing is prior art. All statements as to the date or representation as to the contents of these documents is based on subjective characterization of information available to the applicant, and does not constitute any admission as to the accuracy of the dates or contents of the documents.

SUMMARY OF THE INVENTION

The present invention provides, inter alia, an elastase-resistant ATIII, comprising an ATIII comprising a compound of Formula I at residues 389 and 390:

D-E

Formula I wherein D is selected from the group consisting of: glutaric acid; phenylalanine; glycine; and proline; and E is selected from the group consisting of alanine; phenylalanine; glycine; and proline;

or a pharmaceutically-acceptable formulation thereof.

Preferred are elastase-resistant ATIIIs as described above, which further comprise a compound of Formula II at residues 386–388 and a compound of Formula V at residue 391,

A-B-C

Formula II wherein A is selected from the group consisting of: threonine; and glutamic acid, and wherein B is selected from the group consisting of: alanine; glutamic acid; and glutamine, and wherein C is selected from the group consisting of: leucine; valine; glycine; glutamic acid, and threonine, and

F

Formula III wherein F is selected from the group consisting of: alanine; isoleucine; serine; glycine; and asparagine.

Those ATIIIs having enhanced-heparin affinity are preferred, particularly those, wherein said ATIII has enhanced heparin affinity by virtue of a mutation two residues subsequent to a glycosylation site.

In particular, preferred are elastase-resistant ATIIIs as described above, wherein D is glutamic acid and E is alanine, wherein D is glutamic acid and E is glycine, or D is phenylalanine and E is phenylalanine.

Those wherein D is glutamic acid and E is alanine and
wherein A is threonine, B is glutamic acid, C is glycine and F is serine, or
wherein A is threonine, B is glutamic acid, C is valine and F is alanine, or
wherein A is threonine, B is alanine, C is leucine and F is isoleucine are most preferred.

However, those wherein D is glutamic acid and E is glycine and wherein A is threonine, B is glutamic acid, C is leucine and F is alanine are also preferred.

However, those wherein wherein D is phenylalanine and E is phenylalanine and
wherein A is threonine, B is glutamic acid, C is glycine and F is serine are also most preferred.

Also provide are elastase-resistant ATIIIs comprising an amino acid sequence at residues 386 through 391 selected from the group consisting of: SEQ ID NO 1; SEQ ID NO 2; SEQ ID NO 3; SEQ ID NO 4; SEQ ID NO 5; SEQ ID NO 6; SEQ ID NO 7; SEQ ID NO 8; SEQ ID NO 9; SEQ ID NO 10; SEQ ID NO 11; SEQ ID NO 12; SEQ ID NO 13; and SEQ ID NO 14; and SEQ ID NO 15, or a pharmaceutically-acceptable formulation thereof.

Nucleic acid molecules comprising a nucleic acid molecule which encodes the present ATIIIs are also provided by the present invention. In particular, there are provided nucleic acids encoding the present ATIIIs, wherein said ATIIIs comprise, at residues 386 through 391, an amino acid sequence selected the group consisting of; SEQ ID NO 1; SEQ ID NO 2; SEQ ID NO 3; SEQ ID NO 4; SEQ ID NO 5; SEQ ID NO 6; SEQ ID NO 7; SEQ ID NO 8; SEQ ID NO 9; SEQ ID NO 10; SEQ ID NO 11; SEQ ID NO 12; SEQ ID NO 13; and SEQ ID NO 14; and SEQ ID NO 15.

Methods are also provided herein. In particular, there are provided methods to inhibit thrombin activation, comprising administering an ATIII (of the present invention. In one embodiment, there are provided methods to inhibit thrombin activation in a patient in need of such inhibition, comprising administering an ATIII of the present invention. Preferred methods utilize the preferred and most preferred ATIIIs.

Also provided are methods to inhibit factor Xa in a patient in need of such inhibition, comprising administering an ATIII of the present invention. Preferred methods utilize those ATIIIs with factor Xa-inhibiting activity as specifically described in the examples.

Also provided are methods to inhibit thrombin in a patient in need of such inhibition, comprising administering an ATIII of the present invention. Preferred methods utilize those ATIIIs with thrombin inhibiting activity as specifically described in the examples.

The present invention also provides methods to treat and/or reduce the risk of thrombin activation-related pathological symptoms in a patient in need of such treatment, comprising administering the presently-disclosed ATIIIs. In particular, methods to treat the pathological symptoms due to sepsis; trauma; acute respiratory distress syndrome; thrombosis; stroke; and restenosis are preferred. In addition, methods wherein the thrombin activation-related pathological symptom is a risk such as: reocclusion and restenosis in percutaneous transluminal coronary angioplasty; thrombosis associated with surgery; ischemia/reperfusion injury; and coagulation abnormalities in cancer or surgical patients is herein provided. In particular, methods as described in this paragraph, wherein the coagulation abnormalities associated with surgical patients are those associated with cardiopulmonary bypass or joint replacement are preferred.

Also provided are methods to reduce the risk of thrombosis, restenosis, reocclusion, and coagulation abnormalities in a patient in need of such reduction, comprising administering a compound herein, preferrably a most preferred compound, or a nucleic acid which encodes therefor. In particular, methods as described in this paragraph, wherein the coagulation abnormalities are those associated with cardiopulmonary bypass or joint replacement are preferred.

Also provided are methods to treat sepsis, trauma, acute respiratory distress syndrome, disseminated intravascular coagulopathy, ischemic stroke, thrombosis, restenosis, and reocclusion in a patient in need of such treatment, comprising administering a compound herein, preferrably a most preferred compound, or a nucleic acid which encodes therefor.

Lastly, the present invention also provides methods for producing elastase-resistant human antithrombin III in bodily fluid, comprising: producing a transgenic animal that expresses in bodily fluid a transgene which encodes an elastase-resistant ATIII of the present invention, wherein the human antithrombin III is secreted into the bodily fluid produced by the transgenic animal; . . . collecting bodily fluid from the transgenic animal, which bodily fluid contains the human antithrombin III; and isolating the human antithrombin III from the collected bodily fluid. Preferred are methods wherein the bodily fluid is selected from the group consisting of; milk or urine. Those methods wherein the bodily fluid is milk and the animal is selected from the group consisting of: goat; sheep; and cow are more preferred. Most preferred are methods for producing human antithrombin III in goat milk, comprising: producing a transgenic goat that expresses in mammary tissue a transgene which encodes an elastase-resistant ATIII of the present invention, wherein the human antithrombin III is secreted into the milk produced by the transgenic goat; collecting milk from the transgenic goat which milk contains the human antithrombin III; and isolating the human antithrombin III from the collected milk.

DEFINITIONS

"Allelic variant" is meant to refer to a full length gene or partial sequence of a full length gene that occurs at essentially the same locus (or loci) as the referent sequence, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions).

"Antibody" as used herein includes both polyclonal and monoclonal antibodies as well as fragments thereof, such as Fv, Fab and F(ab)$_2$ fragments that are capable of binding antigen or hapten.

"at residue" or "at residues" means the location as indicated by the number system for naturally-occurring ATIII as described in Bock et al., (1982) *Nucleic Acids Res.*, 10, 81 138–125.

"ATIII target enzyme(s)" means any enzyme which is inhibited by ATIII, including enzymes in the intrinsic and extrinsic coagulation pathway, for example, thrombin, factor Xa, factor IXa, factor XIa, factor XIIa, kallikrein, TF-VIIa.

"Thrombin" means any thrombin molecule recognized in the art, including the mutants or allelic variants, or any such new molecules discovered.

"antithrombin-associated response" means not only any humoral or cellular immune response, but also any biological response resulting from an interaction with antithrombin.

"Fragment" is meant to refer to any subset of the referent protein or nucleic acid molecule.

"enhanced-heparin affinity ATIII" means any ATIII with the ability to bind heparin with Kds less than that of plasma-derived ATIII (alpha isoform), including for example, modified ATIIIs such as described in U.S. Pat. Nos. 5,618,713 and 5,700,663, those derived from wild type β-ATT, or those wherein glycosylation at one or more residues, ie Asn at 135, has been prevented via a secondary mutation, ie. replacement of serine residue 137 with any other amino acid except threonine or cysteine.

"Proteins" means any compounds which comprise amino acids, including peptides, polypeptides, fusion proteins, etc.

Moreover, for the purposes of the present invention, the term "a" or "an" entity refers to one or more of that entity, for example, "a protein" or "a nucleic acid molecule" refers to one or more of those compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds. According to the present invention, an isolated, or biologically pure, protein or nucleic acid molecule is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis.

DETAILED DESCRIPTION OF THE INVENTION

For the purposes of the present invention, the attributing of numbers to ATIII residues is based on the numbering convention commonly recognized in the art. The convention utilizes Bock et al., (1982) *Nucleic Acids Res.*, 10, 8113–8125 as the reference sequence, and descriptions of residue location are based on the reference sequence rather than on the resultant modified sequence. Deletions of amino acid(s) are normally designated by a delta symbol (Δ). Insertions are normally designated by the amino acid residue number preceding the insertion, and then by a letter designation. For example, insertion of a tripeptide sequence after residue 336 would be designated 336A, 336B, 336C. It is not typical nor intended in this disclosure, to alter this convention.

Moreover, "a compound of Formula X at residue(s) Y" means that the compound of Formula X is in position Y, and replaces any residue(s) at position Y. It is not meant that the compound is in addition to any residue which was formerly in position Y; on the contrary, the compound is instead of, or takes the place of, any residue that was in position Y. In this definition, "X" and "Y" are used as variables, and are used in the claims, for example, as "a compound of Formula I at residues 389 and 390". In that instance, a compound of Formula I is a dimer and replaces naturally-occurring residues at 389 and 390.

The present invention provides, inter alia, an elastase-resistant ATIII, comprising an ATIII comprising a compound of Formula I at residues 389 and 390:

D-E

Formula I wherein D is selected from the group consisting of: glutamic acid; phenylalanine; glycine; and proline; and E is selected from the group consisting of: alanine; phenylalanine; glycine; and proline;

or a pharmaceutically-acceptable formulation thereof.

Preferred are elastase-resistant ATIIIs as described above, which further comprise a compound of Formula II at residues 386–388 and a compound of Formula III at residue 391,

A-B-C

Formula II wherein A is selected from the group consisting of: threonine; and glutamic acid, and wherein B is selected from the group consisting of: alanine; glutamic acid; and glutamine, and wherein C is selected from the group consisting of: leucine; valine; glycine; glutamic acid, and threonine, and

F

Formula III wherein F is selected from the group consisting of: alanine; isoleucine; serine; glycine; and asparagine.

Those ATIIIs having enhanced-heparin affinity are preferred, particularly those, wherein said ATIII has high heparin affinity by virtue of a mutation two residues subsequent to a glycosylation site.

In particular, preferred are elastase-resistant ATIIIs as described above, wherein D is glutamic acid and E is alanine, wherein D is glutamic acid and E is glycine or D is phenylalanine and E is phenylalanine.

Those wherein D is glutamic acid and E is alanine and
 wherein A is threonine, B is glutamic acid, C is glycine and F is serine, or
 wherein A is threonine, B is glutamic acid, C is valine and F is alanine, or
 wherein A is threonine, B is alanine, C is leucine and F is isoleucine are most preferred.

However, those wherein D is glutamic acid and E is glycine and wherein A is threonine, B is glutamic acid, C is leucine and F is alanine are also preferred.

However, those wherein wherein D is phenylalanine and E is phenylalanine and wherein A is threonine, B is glutamic acid, C is glycine and F is serine are also most preferred.

Also provided are elastase-resistant ATIIIs comprising an amino acid sequence at residues 386 through 391 selected from the group consisting of: SEQ ID NO 1; SEQ ID NO 2; SEQ ID NO 3; SEQ ID NO 4; SEQ ID NO 5; SEQ ID NO 6; SEQ ID NO 7; SEQ ID NO 8; SEQ ID NO 9; SEQ ID NO 10; SEQ ID NO 11; SEQ ID NO 12; SEQ ID NO 13; and SEQ ID NO 14; and SEQ ID NO 15, or a pharmaceutically-acceptable formulation thereof.

There are also provided recombinant cells comprising the proteins herein described.

An elastase-resistant ATIII protein of the present invention, including a homolog, can be identified in a straight-forward manner by the protein's ability to resist cleavage by elastase and to inhibit an ATIII target enzyme.

Elastase-resistant ATIII protein homologs can be the result of natural allelic variation or natural mutation. Elastase-resistant ATIII protein homologs of the present invention can also be produced using techniques known in the art including, but not limited to, direct modifications to the protein or modifications to the gene encoding the protein using, for example, classic or recombinant nucleic acid techniques to effect random or targeted mutagenesis.

One embodiment of an elastase-resistant ATIII protein of the present invention is a fusion protein that includes an elastase-resistant ATIII protein domain attached to one or more fusion segments. Suitable fusion segments for use with the present invention include, but are not limited to, segments that can: enhance a protein's stability and/or assist purification of an elastase-resistant ATIII protein (e.g., by affinity chromatography). A suitable fusion segment can be a domain of any size that has the desired function (e.g., imparts increased stability, imparts increased immunogenicity to a protein, and/or simplifies purification of a protein). Fusion proteins are preferably produced by culturing a recombinant cell transformed with a fusion nucleic acid molecule that encodes a protein including the fusion segment attached to either the carboxyl and/or amino terminal end of an elastase-resistant ATIII-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); a "tag" domain (e.g., at least a portion of β-galactosidase, a strep tag peptide, other domains that can be purified using compounds that bind to the domain, such as monoclonal antibodies); and/or a linker and enzyme domain (e.g., line phosphatase domain connected to an elastase-resistant ATIII protein by a linker). More preferred fusion segments include metal binding domains, such as a poly-histidine segment; a maltose binding domain; a strep tag peptide; and a phage T7 S10 peptide.

An elastase-resistant ATIII molecule of the present invention can also include chimeric molecules comprising an elastase-resistant ATIII molecule and a second molecule that enables the chimeric molecule to be bound to a surface in such a manner that the elastase-resistant ATIII molecule inhibits an ATIII-target enzyme in essentially the same manner as an elastase-resistant ATIII molecule that is not bound to a surface. An example of a suitable second molecule includes a portion of an immunoglobulin molecule or another ligand that has a suitable binding partner that can be immobilized on a substrate, e.g., biotin and avidin, or a metal-binding protein and a metal (e.g., His), or a sugar-binding protein and a sugar (e.g., maltose).

A variety of procedures known in the art may be used to molecularly alter naturally-occurring or synthetic ATIII so as to produce an elastase-resistant ATIII of the present invention.

Nucleic acid molecules comprising a nucleic acid molecule which encodes the present ATIIIs are also provided by the present invention. In particular, there are provided nucleic acids encoding the present ATIIIs, wherein said ATIIIs comprise, at residues 386 through 391, an amino acid sequence selected the group consisting of: SEQ ID NO 1; SEQ ID NO 2; SEQ ID NO 3; SEQ ID NO 4; SEQ ID NO 5; SEQ ID NO 6; SEQ ID NO 7; SEQ ID NO 8; SEQ ID NO 9; SEQ ID NO 10, SEQ ID NO 11; SEQ ID NO 12; SEQ ID NO 13; and SEQ ID NO 14; and SEQ ID NO 15.

The present invention also comprises expression vectors and recombinant cells comprising the present nucleic acid molecules. Also provided are fusion proteins constructed using the present nucleic acid compounds.

Included within the scope of the present invention, with particular regard to the nucleic acids above, are allelic variants, degenerate sequences and homologues. Allelic variants are well known to those skilled in the art and would be expected to be found within a given diploid organism and/or among a group of organisms. The present invention also includes variants due to laboratory manipulation, such as, but not limited to, variants produced during polymerase chain reaction amplification or site-directed mutagenesis. It is also well known that there is a substantial amount of redundancy in the various codons which code for specific amino acids. Therefore, this invention is also directed to those nucleic acid sequences which contain alternative codons which code for the eventual translation of the identical amino acid. Also included within the scope of this invention are mutations either in the nucleic acid sequence or the translated protein which do not substantially alter the ultimate physical properties of the expressed protein. For example, substitution of valine for leucine, arginine for lysine, or asparagine for glutamine may not cause a change in functionality of the polypeptide.

Knowing the nucleic acid sequences of certain elastase-resistant ATIII nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain ATIII nucleic acid molecules from other species. Such nucleic acid molecules can be obtained in a variety of ways including screening appropriate expression libraries with antibodies of the present invention; traditional cloning techniques using oligonucleotide probes of the present invention to screen appropriate libraries of DNA; and PCR amplification of appropriate libraries or DNA using oligonucleotide primers of the present invention. Preferred libraries to screen or from which to amplify nucleic acid molecules include livestock (cattle, horse, pig) and companion animal (dog and cat) cDNA libraries as well as genomic DNA libraries. Similarly, preferred DNA sources to screen or from which to amplify nucleic acid molecules include adult cDNA and genomic DNA. Techniques to clone and amplify genes are disclosed, for example, in Sambrook et al., ibid.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is, nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulation of the ATIII nucleic acid molecules of the present invention.

One type of recombinant vector, referred to herein as a recombinant molecule, comprises a nucleic acid molecule of the present invention operatively linked to an expression vector. The phrase "operatively linked" refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, insect, other animal, and plant cells. Preferred expression vectors of the present invention can direct gene expression in bacterial, yeast, insect and mammalian cells and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect and mammalian cells, such as, but not limited to, tac, lac, trp, trc, oxy-pro, omp/lpp, rrnB, bacteriophage lambda (such as lambda $P_L$ and lambda $p_R$ and fusions that include such promoters), bacteriophage T7, T7lac, bacteriophage T3, bacteriophage SP6, bacteriophage SP01, metallothionein, alpha-mating factor, *Pichia* alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally-occurring transcription control sequences naturally associated with humans. The present invention also comprises expression vectors comprising a nucleic acid molecule described herein.

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Also provided by the present invention are recombinant cells transformed with a nucleic acid described herein.

Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing ATIII of the present invention or can be capable of producing such proteins after being transformed with at least one nucleic acid molecule of the present invention. Host cells of the present invention can be any cell capable of producing at least one protein of the present invention, and include bacterial, fungal (including yeast), other insect, other animal and plant cells. Preferred host cells include bacterial, mycobacterial, yeast, parasite, insect and mammalian cells. More preferred host cells include *Salmonella, Escherichia, Bacillus, Listeria, Saccharomyces, Spodoptera, Mycobacteria, Trichoplusia*, BHK (baby hamster kidney) cells, COS (e.g., COS-7) cells, and Vero cells. Particularly preferred host cells are *Escherichia coli*, including *E. coli* K-12 derivatives; and insect cell systems which utilize baculovirus.

A recombinant cell is preferably produced by transforming a host cell with one or more recombinant molecules, each comprising one or more nucleic acid molecules of the present invention operatively linked to an expression vector containing one or more transcription control sequences. The phrase "operatively linked" refers to insertion of a nucleic acid molecule into an expression vector in a manner such that the molecule is able to be expressed when transformed into a host cell.

A recombinant cell of the present invention includes any cell transformed with at least one of any nucleic acid molecule of the present invention. Suitable and preferred nucleic acid molecules as well as suitable and preferred recombinant molecules with which to transform cells are disclosed herein.

The translation of the RNA into a peptide or a protein will result in the production of at least a portion of the ATIII protein which can be identified, for example, by the activity of ATIII protein or by immunological reactivity with an anti-ATIII antibody. In this method, pools of mRNA isolated from ATIII-producing cells can be analyzed for the presence of an RNA which encodes at least a portion of the ATIII protein. Further fractionation of the RNA pool can be done to purify the ATIII RNA from non-ATIII RNA. The peptide or protein produced by this method may be analyzed to provide amino acid sequences which in turn are used to provide primers for production of ATIII cDNA, or the RNA used for translation can be analyzed to provide nucleotide sequences encoding ATIII and produce probes for the-production of ATIII cDNA. These methods are known in the art and can be found in, for example, Sambrook, J., Fritsch, E. F., Maniatis, T. in *Molecular Cloning: A Laboratory Manual, Second Edition*, Cold Spring Harbor Laboratory Press, Cold Spring Harbor, N.Y. 1989.

Other types of libraries, as well as libraries constructed from other cells or cell types, may be useful for isolating ATIII-encoding DNA Other types of libraries include, but are not limited to, cDNA libraries derived from other mammals or cell lines derived from other mammals, and genomic DNA libraries. Preparation of cDNA libraries can be performed by standard techniques. Well known cDNA library construction techniques can be found in, for example, Sambrook J., et al., *ibid.*

In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce an elastase-resistant ATIII protein of the present invention. Such a medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane. The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit few impurities.

In addition, recombinant ATIII can be separated from other cellular proteins by use of an immunoaffinity column made with monoclonal or polyclonal antibodies specific for ATIII, or polypeptide fragments of ATIII.

The present invention also includes isolated (i.e., removed from their natural milieu) antibodies that selectively bind to an elastase-resistant portion of the ATIII protein of the present invention or a mimetope thereof (ie., anti- ATIII antibodies). As used herein, the term "selectively binds to" an elastase- resistant portion of the ATIII protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., *ibid*. An anti- elastase-resistant ATIII antibody preferably selectively binds to an elastase- resistant ATIII protein in such a way as to reduce the activity of-that protein. These antibodies may be admixed or conjugated with additional materials, such as cytotic agents or other antibody fragments.

Isolated antibodies of the present invention can include antibodies in a bodily fluid (such as, but not limited to, serum), or antibodies that have been purified to varying degrees. Antibodies of the present invention can be polyclonal or monoclonal. Functional equivalents of such antibodies, such as antibody fragments and genetically- engineered antibodies (including single chain antibodies or chimeric antibodies that can bind to more than one epitope) are also included in the present invention.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce elastase-resistant ATIII proteins of the present invention.

Compositions of the present invention can be administered to any animal having at least one ATIII-target enzyme that can be inhibited by a therapeutic compound of the present invention or by a protein expressed by a nucleic acid molecule contained in a therapeutic composition. Preferred animals to treat are humans, although other mammals, such as cattle, pigs, sheep, horses, cats, dogs, and other pets, work and/or economic food animals are also within the scope of the present invention.

Therapeutic compositions of the present invention can be formulated in an excipient that the animal to be treated can tolerate, Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, cresols, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

Administration of the present compounds can be by a variety of routes known to those skilled in the art including, but not limited to, subcutaneous, intradermal, intravenous, intranasal, oral, transdermal, intramuscular routes and other parenteral routes.

In one embodiment of the present invention, a therapeutic composition can include an adjuvant. Adjuvants are agents that are capable of increasing the immune response of an animal to a specific antigen. Protein adjuvants of the present invention can be delivered in the form of the protein themselves or of nucleic acid molecules encoding such proteins using the methods described herein.

In another embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

Another embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of an animal at a constant rate sufficient to attain therapeutic dose levels of the composition to reduce thrombin-activation and thrombin-mediated biological responses in the animal. The therapeutic composition is preferably released over a period of time ranging from about 1 day to about 12 months, and include release over a 2, 3, 4, 5, 6, 7 day through a 30 day time period.

Acceptable protocols to administer therapeutic compositions of the present invention in an effective manner include individual dose size, number of doses, frequency of dose administration, and mode of administration. Determination of such protocols can be accomplished by those skilled in the art. A suitable single dose is a dose that is capable of protecting (i.e., preventing or treating) an animal from disease when administered one or more times over a suitable time period. The need for additional administrations of a therapeutic composition can be determined by one of skill in the art in accordance with the given condition of a patient.

According to one embodiment, a nucleic acid molecule of the present invention can be administered to an animal in a fashion to enable expression of that nucleic acid molecule into an elastase-resistant ATIII protein in the animal. Nucleic acid molecules can be delivered to an animal in a variety of methods including, but not limited to, (a) administering a naked (i.e., not packaged in a viral coat or cellular membrane) nucleic acid molecule (e.g., as naked DNA molecules, such as is taught, for example in Wolff et al., 1990, *Science* 247, 1465–1468) or (b) administering a nucleic acid molecule packaged as a recombinant virus or as a recombinant cell (i.e., the nucleic acid molecule is delivered by a viral or cellular vehicle).

A naked nucleic acid molecule of the present invention includes a nucleic acid molecule of the present invention and preferably includes a recombinant molecule of the present invention that preferably is replication, or otherwise amplification, competent A naked nucleic acid of the present invention can comprise one or more nucleic acid molecules of the present invention in the form of, for example, a bicistronic recombinant molecule having, for example one or more internal ribosome entry sites. Preferred naked nucleic acid molecules include at least a portion of a viral genome (i.e., a viral vector). Preferred viral vectors include those based on alphaviruses, poxviruses, adenoviruses, herpesviruses, picornaviruses, and retroviruses, with those based on alphaviruses (such as Sindbis or Semliki virus), species-specific herpes iruses and species-specific poxviruses being particularly preferred. Any suitable transcription control sequence can be used, including those disclosed as suitable for protein production. Particularly preferred transcription control sequence include cytomegalovirus intermediate early (preferably in conjunction with Intron-A), Rous Sarcoma Virus long terminal repeat, and tissue-specific transcription control sequences, as well as transcription control sequences endogenous to viral vectors if viral vectors are used. The incorporation of "strong" poly(A) sequences are also preferred.

Naked nucleic acid molecules of the present invention can be administered by a variety of methods. Suitable delivery methods include, for example, intramuscular injection, subcutaneous injection, intradermal injection, intradermal scarification, particle bombardment, oral application, and nasal application, with intramuscular injection, intradermal injection, intradermal scarification and particle bombardment being preferred. A preferred single dose of a naked DNA molecule ranges from about 1 nanogram (ng) to about 1 milligram (mg), depending on the route of administration and/or method of delivery, as can be determined by those skilled in the art. Examples of administration methods are disclosed, for example, in U.S. Pat. No. 5,204,253, by Bruner, et al., issued Apr. 20, 1993, PCT Publication No. WO 95/19799, published Jul. 27, 1995, by McCabe, and PCT Publication No. WO 95/05853, published Mar. 2, 1995, by Carson, et al. Naked DNA molecules of the present invention can be contained in an aqueous excipient (e.g., phosphate buffered saline) and/or with a carrier (e.g., lipid-based vehicles), or it can be bound to microparticles (e.g., gold particles).

A recombinant virus of the present invention includes a recombinant molecule of the present invention that is packaged in a viral coat and that can be expressed in an animal after administration. Preferably, the recombinant molecule is packaging-deficient and/or encodes an attenuated virus. A number of recombinant viruses can be used, including, but not limited to, those based on alphaviruses, poxviruses, adenoviruses, herpesviruses, picornaviruses and retroviruses.

When administered to an animal, a recombinant virus of the present invention infects cells within the recipient animal and directs the production of a protein molecule that is capable of reducing thrombin-activation and/or thrombin-activation and/or thrombin-mediated biological responses in the animal. For example, a recombinant virus comprising an elastase-resistant ATIII nucleic acid molecule of the present invention is administered according to a protocol that results in the animal producing an amount of protein sufficient to reduce thrombin-mediated biological responses. Administration protocols are similar to those described herein for protein-based compositions, with subcutaneous, intramuscular, intranasal and oral administration routes being preferred.

Pharmaceutically useful compositions comprising elastase-resistant ATIII DNA or elastase-resistant ATIII protein, may be formulated according to known methods such as by the admixture of a pharmaceutically acceptable carrier, or by modification with additional chemical moieties so as to form a chemical derivative. Examples of such carriers, modifications and methods of formulation may be found in Remington's Pharmaceutical Sciences. To form a pharmaceutically acceptable composition suitable for effective administration, such compositions will contain an effective amount of the protein or DNA.

The present invention also has the objective of providing suitable topical, oral, systemic and parenteral formulations of the pharmaceutical compounds herein provided. The formulations can be administered in a wide variety of therapeutic dosage forms in conventional vehicles for administration. For example, the compounds can be formulated for oral administration in the form of tablets, capsules (each including timed release and sustained release formulations), pills, powders, granules, elixirs, tinctures, solutions, suspensions, syrups and emulsions, or by injection. Likewise, they may also be administered intravenously (both bolus and infusion), during angioplasty/catheterization, intraperitoneally, subcutaneously, topically with or without occlusion, or intramuscularly, all using forms well known to those of ordinary skill in the pharmaceutical arts.

An elastase-resistant ATIII molecule can be combined with a buffer in which the elastase-resistant ATIII molecule is solubilized, and/or with a carrier. Suitable buffers and carriers are known to those skilled in the art. Examples of suitable buffers include any buffer in which an elastase-resistant ATIII molecule can function to inhibit its target enzyme(s), such as, but not limited to, phosphate buffered saline, water, saline, phosphate buffer, bicarbonate buffer, HEPES buffer (N-2-hydroxyethylpiperazine-N'-2ethanesulfonic acid buffered saline), TES buffer (Tris-EDTA buffered saline), Tris buffer and TAE buffer (Tris-acetate-EDTA). Examples of carriers include, but are not limited to, polymeric matrices, toxoids, and serum albumins, such as bovine serum albumin.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water, and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol waxes and the like. Lubricants used in these dosage forms include, without limitation, sodium oleate, sodium stearate, magnesium stearate, sodium benzoate, sodium acetate, sodium chloride, and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methylcellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions formulations. The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans polycyanoacrylates and cross-linked or amphipathic block copolymers of hydrogels.

Therefore, methods are also provided herein, which utilize the compounds, formulations, compositions and protocols described above. In particular, there are provided methods to inhibit thrombin activation, comprising administering an ATIII of the present invention. In one embodiment, there are provided methods to inhibit thrombin activation in a patient in need of such inhibition, comprising administering an ATIII of the present invention. Preferred methods utilize the preferred and most preferred ATIIIs.

Also provided are methods to inhibit factor Xa in a patient in need of such inhibition, comprising administering an ATIII of the present invention. Preferred methods utilize those ATIIIs with factor Xa-inhibiting activity as specifically described in the examples.

Also provided are methods to inhibit thrombin in a patient in need of such inhibition, comprising administering an ATIII of the present invention. Preferred methods utilize those ATIIIs with thrombin inhibiting activity as specifically described in the examples.

The present invention also provides methods to treat and/or reduce the risk of thrombin activation-related and/or thrombin-mediated pathological symptoms in a patient in need of such treatment, comprising administering the presently-disclosed ATMs. In particular, methods to treat the pathological symptoms due to sepsis; trauma; acute respiratory distress syndrome; thrombosis; stroke; and restenosis are preferred. In addition, methods wherein the thrombin activation- and/or thrombin mediated- related pathological symptom is a risk such as:reocclusion and restenosis in percutaneous transluminal coronary angioplasty, thrombosis associated with surgery, ischemia/reperfusion injury; and coagulation abnormalities in cancer or surgical patients is herein provided. In particular, methods as described in this paragraph, wherein the coagulation abnormalities associated with surgical patients are those associated with cardiopulmonary bypass and joint replacement are preferred.

Also provided are methods to reduce the risk of thrombosis, restenosis, reocclusion, and coagulation abnormalities in a patient in need of such reduction, comprising administering a compound herein, preferrably a most preferred compound, or a nucleic acid which encodes therefor. In particular, methods as described in this paragraph, wherein the coagulation abnormalities are those associated with cardiopulmonary bypass are preferred.

Also provided are methods to treat sepsis, trauma, acute respiratory distress syndrome, disseminated intravascular coagulopathy, ischemic stroke, thrombosis, restenosis, and reocclusion in a patient in need of such treatment, comprising administering a compound herein, preferrably a most preferred compound, or a nucleic acid which encodes therefor.

Lastly, the present invention also provides methods for producing elastase-resistant human antithrombin III in bodily fluid, comprising: producing a transgenic animal that expresses in bodily fluid a transgene which encodes an elastase-resistant ATIII of the present invention, wherein the human antithrombin III is secreted into the bodily fluid produced by the transgenic animal; collecting bodily fluid from the transgenic animal, which bodily fluid contains the human antithrombin III; and isolating the human antithrombin III from the collected bodily fluid. Preferred are methods wherein the bodily fluid is selected from the group consisting of: milk or urine. Those methods wherein the bodily fluid is milk and the animal is selected from the group consisting of: goat; sheep; and cow are more preferred. Most preferred are methods for producing human antithrombin III in goat milk, comprising: producing a transgenic goat that expresses in mammary tissue a transgene which encodes an elastase-resistant ATIII of the present invention, wherein the human antithrombin III is secreted into the milk produced by the transgenic goat; collecting milk from the transgenic goat which milk contains the human antithrombin III and isolating the human antithrombin III from the collected milk. This aspect of the invention can be accomplished according to U.S. patent Ser. No. 5,843,705, which patent is hereby incorporated by reference in its entirety.

The present invention also provides methods to identify the ability of a test compound to interfere with the present ATIII/thrombin and/or ATIII interaction, comprising: contacting the test compound with a protein of the present invention; and determining whether the test compound and said protein interact.

The following examples illustrate the present invention without, however, limiting it. It is to be noted that the Examples include a number of molecular biology, microbiology, immunology and biochemistry techniques considered to be known to those skilled in the art. Disclosure of such techniques can be found, for example, in Sambrook et al., ibid., and related references.

EXAMPLES

Example 1

Materials Used in Preparation and Assay of Modified AtIIIs

Plasmids

Modified ATIII sequences were derived from the antithrombin III cDNA insert of the pBlueBac baculovirus expression construct, BB.ATIII.N135A (Ersdal-Badju et al., 310 *Biochem. J.* 323 (1995)). The 1500 bp EcoRI-Bam HI ATIII.N135A cDNA insert of BB.ATIII.N135A in pUC19 (B1) was used as the template DNA for PCR mutagenesis reactions.

Baculovirus transfer plasmid pBlueBac2 was purchased from Invitrogen (San Diego, Calif.) and used for expression of Group I mutants. pBlueBac2 contains the *Autographa californica* nuclear polyhedrosis virus polyhedrin promoter, a replication origin, an ampicillin drug resistance marker, and an ETL/β-galactosidase expression unit to facilitate identifying recombinant viruses. In addition, pBlueBac2 contains baculovirus DNA sequences which flank the polyhedrin and β-galactosidase transcription units and promote homologous recombination between the transfer plasmid and the baculovirus genome. pBlueBac2 transfer plasmid constructs containing Group I ATIII sequences were purified on Qiagen columns prior to co-transfection of Sf9 cells with linearized baculovirus DNA.

The pFastBac1 baculovirus transfer plasmid was obtained as part of Bac-to-Bac™ Baculovirus Expression System (Gibco/BRL, Gaithersburg, Md.) and used for expression of Group II mutants (see Table 2). pFastBac1 carries a mini-Tn7 transposon which contains an expression cassette consisting of a gentamicin resistance marker and the baculovirus polyhedrin promoter interposed between the left and right arms of Tn7. This mini-Tn7, along with a helper plasmid (pMON7124) present in *E. coli* DH10Bac cells, facilitates insertion of the recombinant sequences into the mini-attTn7 present on the baculovirus shuttle vector (bacmid, bMON14272), also present in the DH10Bac cells. "Miniprep" DNAs of pFast Group II transfer plasmids were used without further purification for transfection of DH10Bac *E. coli*.

Oligonucleotides

Mutagenic oligonucleotides were custom synthesized by Gibco/BRL and received deprotected, desalted and lyophilized. They were reconstituted in sterile deionized water prior to use. Synthetic oligonucleotide sequences are listed in Table 2. In addition to containing codon changes for specifying amino acid substitutions, most mutagenic oligonucleotide sequences also incorporated translationally silent changes which introduced restriction sites for mutant subclone identification.

The LEAI mutagenic primer corresponds to the noncoding strand of ATIII between nucleotides 1326–1292. In addition to specifying codon changes at the P6–P3 amino acids, the LEAI primer also introduces an Eag I site.

Group I mutagenic oligonucleotides correspond to the ATIII coding strand and start at nucleotide 1298 so as to allow in-frame, blunt-end ligation of mutation-containing PCR fragments to the 244 bp Pst I (1052)- Rsa I (1296) fragment of the ATIII cDNA (see FIG. 1). The downstream primer for Group I PCR mutagenesis reactions was NEB #1233 (New England Biolabs), which is a "universal" M13 "reverse sequencing" primer that hybridizes to the polylinker of the vector for the B1 ATIII.N135A/pUC19 template.

TABLE 2

Oligonucleotides Used for Mutagenesis and Expression of Neutrophil-Resistant ATIIIs Primer Sequence (and position in ATTII cDNA, numbering of (Bock et al., 10 Nucleic Acids Res.8113 (1982))

| | | |
|---|---|---|
| AT3.LEAI nc1327 | -5'-TAGCGAACGGCCGATAGCCTCAAGAGCGGTACTTGC-3' | (SEQ ID NO 34) |
| GROUP I: | | |
| AT.Aa | 1298-5'-ACCGCGGAAGGAGGAGGCGGCCGTTCGCTAAACCCC-3' | (SEQ ID NO 17) |
| AT.FF | 1298-5'-ACCGCTGTTTTCTTCGCCGGCCGTTCGCT-3' | (SEQ ID NO 18) |
| AT.Bb | 1298-5'-ACCGAAGGTTTCTTCTCTGGCCGTTCTTTAAACCCCAACAGGGTGACT-3' | (SEQ ID NO 19) |
| AT.F2A | 1298-5'-ACCCAAACTTTCTTCAACGGCCGAAGCTTAAACCCCAACAGGGTGACT-3' | (SEQ ID NO 20) |
| GROUP II: | | |
| AT.Bb.A | 1290-5'-CTGCAAGTACTGAAGGTGAAGCTTCTGGCCGTTC-3' | (SEQ ID NO 21) |
| AT.Bb.B | 1290-5'-CTGCAAGTACTGAAGGTGAAGGTTCTGGCCGTTC-3' | (SEQ ID NO 22) |

TABLE 2-continued

Oligonucleotides Used for Mutagenesis and Expression of Neutrophil-Resistant
ATIIIs Primer Sequence (and position in ATIII cDNA, numbering of
(Bock et al., 10 Nucleic Acids Res.8113 (1982))

| | | |
|---|---|---|
| AT.Bb.C | 1284-5'-AAGCAGCTGCTAGCGAAGAAGGTGAAGCTTCTGGCCGTTC-3' | (SEQ ID NO 23) |
| AT.Bb.D | 1284-5'-AAGCAGCTGCTAGCGAAGAAGGTGAAGGTTCTGGCCGTTC-3' | (SEQ ID NO 24) |
| AT.13.A | 1290-5'-CTGCAAGTACTGCTGTTGAAGGTGCTGGCCGT-3' | (SEQ ID NO 25) |
| AT.13.B | 1290-5'-CTGCAAGTACTGAGGTTGAAGGTGCTGGCCGT-3' | (SEQ ID NO 26) |
| AT.13.C | 1290-5'-CTGCAAGTACTGAGCTTGAAGGTGCTGGCCGT-3' | (SEQ ID NO 27) |
| AT.13.D | 1290-5'-CTGCAAGTACTGCTCTTGAAGGTGCTGGCCGT-3' | (SEQ ID NO 28) |
| AT.5EA | 1290-5'-CTGCAAGTACTGCTGTTGAGGCTGCTGGCCGT-3' | (SEQ ID NO 29) |
| AT.7EVEA | 1290-5'-CTGCAAGTACTGAGGTTGAGGCTGCTGGCCGT-3' | (SEQ ID NO 30) |

PCR AND SEQUENCING PRIMERS:

| | | |
|---|---|---|
| AT.1201F | 5'-TATTGTTGCAGAAGGCCG-3' | (SEQ ID NO 31) |
| NEB#1201 | 5'-AACAGCTATGACCATG-3 | (SEQ ID NO 32) |
| NEB#1233 | 5'-AGCGGATAACAATTTCACACAGGA-3' | (SEQ ID NO 33) |

Group II mutagenic oligonucleotides also correspond to the ATIII coding strand, and were used as the "M" (mutagenic primer) in the 3-primer PCR mutagenesis protocol of Picard et al, 22 *Nucleic Acids Res.* 2587 (1994) with modifications as described by Picard and Bock, *Methods in Molecular Biology: PCR Protocols* (1996). Primer at3.1201F was used as the "F" forward primer, and M13 "reverse sequencing primer" NEB #1201, corresponding to a universal sequence in the polylinker of the template vector, was used as the "R" reverse primer.

Primer at3.1201F was also used as a primer for verifying DNA sequence in the region of neutrophil-resistant ATIII transfer plasmids that were derived from PCR Molecular Biology Enzymes Restriction endonucleases were purchased from Promega (Madison, Wis.), New England Biolabs (Beverly, Mass.) and Boehringer/Mannheim (Indianapolis, Ind.). T4 DNA kinase and calf alkaline phosphatase (CAP) were purchased from Boehringer/Mannheim. Pfu DNA polymerase was obtained from Strategene (La Jolla, Calif.). Sequenase v2.0 was from USB.

Cells and Medium

E. coli INVaF' cells (EndA1, recA1, hsdR17, r-k, m+k), supE44, lambda-, thi-1, gyrA, re1A1, f80 lacZDM15 D (lacZYA-argF), deoR+, F') were used for propagation of pUC, pBlueBac2 and pFast plasmids and their ATIII-containing derivatives. E. coli DH10Bac cells (containing helper plasmid pMON7124 and bacmid bMON14272) were used for transposition of recombinant bacmid DNA for Group II mutants in the Bac-to-Bac™ Baculovirus Expression System (Gibco/BRL).

Sf9 *Spodoptera frugiperda* cells, originally obtained from Invitrogen, were used as host cells for baculovirus propagation and expression. The Sf9 cells were maintained in serum-free Sf-900 II medium (Gibco/BRL). Erlenmeyer flasks containing Sf9 cells at densities of 1–3×106/mL were maintained at 27° C. and shaken at 160 rpm for oxygenation. Viabilities were >97% by trypan blue exclusion. For transfections (all mutants) and plaque purification (Group I mutants), Sf9 cells were plated in TNM-FH medium (Invitrogen) supplemented with 10% fetal bovine serum (FBS). The Grace's medium and Bluo-Gal also used in these procedures were purchased from Gibco/BRL. For Group I mutants, linear wildtype baculovirus DNA and cationic liposome reagent used for cotransfections of Group I pBlue-Bac transfer plasmids were purchased from Invitrogen.

Antisera

Sheep-anti-human-ATIII and alkaline phosphatase-conjugated-donkey-anti-sheep-Ig were purchased from The Binding Site Ltd. (Birmingham, England).

Electrophoresis and Chromatography

"Regular" polyacrylamide stocks (29:1 acrylamide:bis) were purchased from Amresco (Solon, Ohio). "Duracryl" acrylamide (37.5:1 acrylamide:bis) for Laemmli gels were purchased from ESA, Inc. (Chelmsford, Mass.). "Longranger" acrylamide for DNA sequencing was purchased from AT Biochem (Malvern, Pa.).

All Laemmli electrophoresis was performed on 10×10 cm gels in a Mini-PROTEAN II electrophoresis cell (BioRad). Protein bands were visualized with SYPRO Red (Molecular Probes, Eugene, Oreg.). SYPRO Red stained gels were photographed on a UV transilluminator using Polaroid 667 film.

5 mL Econopak heparin cartridges were purchased from BioRad (Hercules, Calif.). Heparin affinity chromatography was performed using a low pressure Econosystem controller (BioRad).

Buffers

PE: 20 mM phosphate, pH 7.4, 0.1 mM EDTA

PNE: 20 mM sodium phosphate, pH 7.4, 100 mM NaCl, 0.1 mM EDTA

PNE-PEG: 20 mM sodium phosphate, pH 7.4, 100 mM NaCl, 0.1 mM EDTA, 0.1% (w/v) polyethylene glycol 6000

SDS Non-reducing Sample Buffer: 0.125 M Tris-HCl, pH 6.8,20% glycerol, 4% SDS, trace bromophenol blue SDS Reducing Sample Buffer: 0.125 M Tris-HCl, pH 6.8, 20% glycerol, 5% beta-mercaptoethanol 4% SDS, trace bromophenol blue TBE: 0.09 M Tris-Borate, pH 8.0,2 mM EDTA
TBS: 50 mM Tris-HCl, pH 8.0,0.15 M NaCl
TBST: 50 mM Tris-HCl, pH 8.0, 0.15 M NaCl, 0.05% Tween-20
TE: 10 mM Tris-Cl, pH 8.0, 1 mM EDTA
TG-SDS: 25 mM Tris, 192 mM glycine, 0.1% SDS
Chromogenic Substrates S-2238 (H-D-phenylalanyl-L-pipecolyl-L-arginine-p-nitroanalide dihydrochloride) and S-2765 (H-a-benzyloxycarbonyl-D-arginyl-L-glycyl-L-arginine-nitroanalide dihydrochloride) were purchased from Chromogenix, (Molndal, Sweden). MeO-Suc-Ala-Ala-Pr-Val-pNA and Suc-Ala-Ala-Pro-Phe-pNA were purchased from Sigma.

Serine Proteinases and Proteinase Inhibitors

Human α-thrombin preparations were gifts for Dr. John Fenton and Dr. William Lawson (Wadsworth Laboratories, New York State Department of Health, Albany, N.Y.). Human factor Xa and human plasma ATIII were purchased from Enzyme Research Laboratories, Inc. (South Bend, Ind.). Human Leukocyte Elastase and Human Cathepsin G were purchased from Elastin Products Co. (Owensville, Mo.).

Heparin Sodium

Heparin sodium was purchased from Calbiochem. The heparin was derived from porcine intestinal mucosa, ranging from 13,500–15,000 daltons, containing 140 USP Heparin Units per mg.

Example 2

Mutagenesis and Construction of Recombinant Baculoviruses Which Comprise Modified ATIII Modified ATIIIs were generated on a human ATIII.N135A background. The template DNA was B1, which is pUC19 containing a ATIII.N135A cDNA insert (Ersdal-Badju et al., 310 Biochem. J. 323 (1995)).

Group I Mutants

PCR Mutagenesis. For Group I mutants, the 100 µL mutagenesis reactions (in 600 µL PCR tubes) contained 43.2 fmol template DNA (120 ng of 4.2 kb plasmid), 100 pmol (1 µM) each of the mutagenic (M) and downstream (NEB #1233) primers, 2.5 U Pfu DNA polymerase, dXTPs at 0.2 mM, 20 mM Tris-Cl, pH 8.75, 10 mM KCl, 10 mM (NH4)2SO4, 2 mM $MgC_{12}$, 0.1% Triton X-100 and 0.1 g/L BSA. The enzyme was added last, after the other components were thoroughly mixed, and the reactions were overlaid with mineral oil. Polymerase chain reactions was performed with a Perkin-Elmer Cetus Thermal Cycler (Norwalk, Conn.) programmed for 30 cycles of amplification (94° C., 1 min; 45° C., 1 min; 72° C., 2 min), followed by 5 min at 72° C., and holding at 4° C. until analysis.

Subcloning. The finished PCR reaction, containing double stranded DNA corresponding to the final 227 bp of the cDNA ATIII sequence, was subjected to Bam HI restriction digestion and then electrophoresed on a prerun 5% nondenaturing polyacrylamide gel (29:1 acrylamide:bis, 1×TBE, 50 mA, bromophenol blue to bottom) along with 300 ng pUC18-Hinf size markers. The gel was stained with ethidium bromide, and the bands were visualized by UV transillumination. The expected 5'-blunt-end to 3'-Barn HI 227 bp fragment (nucleotides 1298–1525) was identified, excised from the polyacrylamide gel, placed in Speecapor2 dialysis bags. (12,000–14,000 molecular weight cut-off) and electroeluted overnight in 0.1×TBE on ice at 50 mA. The eluent was collected and particulate acrylamide removed by centrifugation. The DNA was extracted with phenol/chloroform, precipitated with absolute ethanol, washed with 80% ethanol, dried and resuspended in 16 µL sterile deionized water.

Concurrently, B1 (h.at3.N135A/pUC19) was digested with Pst L Rsa I and Stu I. The digest was resolved on a prerun 5% nondenaturing polyacrylamide gel and the 244 bp Pst I, Rsa I fragment (nucleotides 1053–1297) excised. The Pst I - Rsa I fragment was electroeluted, phenol/chloroform extracted and then resuspended in sterile deionized water. In addition, a vector was prepared by digesting with Pst I and Bam HI, followed by dephosphorylation with calf alkaline phosphatase.

Plasmids containing the 3' end of the ATIII cDNA were obtained by three-part ligation of (i) the 5'-blunt-end to 3'-Bam HI 227 bp fragment from the PCR mutagenesis reactions, (ii) the Pst I to Rsa I fragment of B1 (nucleotides 1053–1297), and (iii) pUC19/Pst/Bam HI/CAP vector. Ten µL ligation reactions contained 1 unit T4 DNA ligase and were incubated overnight at 4° C. In addition, the following control reactions were run: (+) insert (−) ligase, (−) insert (+) ligase, and (−) insert (−) ligase. Ligated DNAs were transformed into competent E. coli INVaF' cells (see Transformation Method below) and plated on LB agar plates containing ampicillin and X-gal. Plates were incubated overnight at 37° C. For each variant, a minimum of four colonies were picked onto master plates and used to inoculate 5 mL cultures for miniprep DNA (see Miniprep DNA Method below).

Minipreps were rapidly screened for the presence of B1 parental or mutant sequences by digestion with restriction enzymes for sites introduced by the mutagenic primers. Plasmids containing mutant restriction site markers were then sequenced across the PCR-derived Rsa I to stop codon region to verify the presence of desired mutations and absence of unplanned ones. (see DNA Sequencing Method below).

Following sequence verification, the Pst I-Bam HI fragment containing the 3' end of the ATIII cDNA (nucleotides 1053 to 1525) was prepared and gel purified. In addition, the 5' Nhe I-Pst I portion of the ATIII.N135A cDNA sequence from B1 was also prepared and gel purified. Three-part ligations of the 5' and 3' fragments and pBlueBac2/Nhe I/Bam HI/CAP vector were transformed into competent E. coli INVaF' cells. Single colonies were used to inoculate cultures and high purity DNA of the pBlueBac2 transfer plasmids was prepared by the Qiagen method. Qiagen DNA was resuspended in sterile water and the concentration determined at 260 nm. Qiagen DNA for each transfer plasmid was rechecked by restriction digest, and then cotransfected into Sf9 cells with wildtype linear baculovirus DNA.

Cotransfection of pBlueBac2 Transfer Plasmids and Linear Baculovirus DNA. Sf9 monolayers at 70–80% confluency were prepared by seeding 60 mm plates with 2×106 Sf9 cells for at least 30 minutes. A transfection mix containing 1 mL of unsupplemented Grace's medium, 1 µg of linear AcMNPV DNA and 4 µg of the ATIII-containing pBlueBac2 transfer plasmid (Qiagen DNA) was prepared. 20 µL of thoroughly mixed Cationic Liposome Solution was added to the DNA/Grace's medium solution, vigorously vortexed and then incubated at room temperature for 15 minutes. During the incubation, the medium was aspirated from the Sf9 plates and replaced with 2 mL of Grace's medium. The cells were allowed to sit until the tranfection mix incubation was within 2 minutes of completion (approximately 10 minutes). The Grace's medium was removed from the cells and 1 mL of the transfection mix was added dropwise to the 60 mm plate. The plate was incubated on a slow rocking platform for 4 hours. After 4 hours on the rocking platform, 1 mL of complete TNM-FH medium was added to each 60 mm plate and they were transferred to a 27° C. humidified incubator. 48 hours later, "primary lysates" containing a mixture of recombinant baculovirus and wildtype baculovirus were harvested.

Isolation of Recombinant Baculovirus Expressing Group I Mutants. A plaque purification procedure was used to purify recombinant baculovirus from Sf9 cells infected with primary lysates. 60 cm plates were seeded with 2×106 Sf9 cells for 30 minutes. The medium was aspirated and replaced with 1 mL of 10-, 100- and 1000-fold dilutions of the primary lysate in complete TNM-FH medium. The plate was incubated in a 27° C. humidified incubator for 2 hours, then the media was aspirated and replaced with 4 mL of complete Grace's medium. Warm 10% FBS and 2% Bluo-Gal agarose was poured onto the infected Sf9 cell monolayer and allowed to solidify. The plates were placed in boxes containing sterile wet paper towels to maintain a high humidity level and incubated at 27° C. for 4–6 days, when blue plaques appeared. Isolate blue plaques were picked with a 21 gauge needle and transferred to wells of a 24-well plate containing 5×105 Sf9 cells in 0.5 mL TNM-FH. The 24 well plates were incubated in a 27° C. humidified incubator, and at 4–6 days post-infection, the medium containing the secondary lysate virus stock was harvested. Secondary lysates contained cloned recombinant baculoviruses carrying variant ATIII sequences. The presence of expressed ATIII in secondary lysates was verified by Western blotting, and they were used as virus stocks for further work.

Group II Mutants

PCR Mutagenesis. For Group II mutants, 3-primer mutagenesis was performed according to the protocol of Picard et al. (1994) with modifications as described in Picard and Bock (1996). Step 1: The 100 μL mutagenesis reactions (in 600 μL PCR tubes) contained 43.2 fmol template DNA (120 ng of 4.2 kb plasmid), 100 pmol (1 μM) each of the mutagenic (M) and downstream (NEB #1233) primers, 2.5 U Pfu DNA polymerase, dXTPs at 0.2 mM, 20 mM Tris-Ci, pH 8.75, 10 mM KCl, 10 mM (NH4)2SO4, 2 mM MgC12, 0.1% Triton X-100 and 0.1 g/L BSA. The enzyme was added last, after the other components were thoroughly mixed and the reactions were overlaid with mineral oil. Polymerase chain reactions was performed with a Perkin-Elmer Cetus Thermal Cycler (Norwalk, Conn.) programmed for 30 cycles of amplification (94° C., 1 min; 45° C., 1 min; 72° C., 2 min), followed by 5 min at 72° C., and holding at 4° C. until analysis. Step 2: This step is initiated by adding 500 pmol upstream (1201F) primer to the aqueous phase and performing the amplification program described in Step 1. Step 3: 500 pmol downstream primer (NEB #1233) and again using the same amplification program described in Step 1.

Subcloning and Construction of pFast Transfer Plasmids. The finished PCR reaction, containing double stranded DNA was subjected to Nsi I and Xba I restriction digestion and then electrophoresed on a prerun 5% nondenaturing polyacrylamide gel (29:1 acrylamide:bis, 1×TBE, in 50 mA, bromophenol blue to bottom) along with 300 ng pUC18-Hinf size markers. The gel was stained with ethidium bromide, and the bands were visualized by UV transillumination. The desired 300 bp 5'-Nsi I to 3'-Xba I fragments were identified, excised from the polyacrylamide gel, placed in a Spectapor2 dialysis bags (12,000–14,000 molecular weight cut-off) and electroeluted overnight in 0.1×TBE on ice at 50 mA. The eluent was collected and particulate acrylamide removed by centrifugation. The DNA was extracted with phenol/chloroform, precipitated with absolute ethanol washed with 80% ethanol, dried and resuspended in 16 μL sterile deionized water.

The 300 bp Nsi I/Xba I fragments from the PCR mutagenesis reactions were ligated to pFast*.N135A/Nsi I/Xba I/CAP. Ten μL ligation reactions contained 1 unit T4 DNA ligase and were incubated overnight at 4° C. In addition, the following control reactions were run: (+) insert (–) ligase, (–) insert (+) ligase, and (–) insert (–) ligase. Ligated DNAs were transformed into competent *E. coli* INVaF' cells (see Transformation Method below) and plated on LB agar plates containing ampicillin and X-gal. Plates were incubated overnight at 37° C. For each variant, a minimum of four white (insert-containing) colonies were picked onto master plates and used to inoculate 5 mL cultures for miniprep DNA (see Miniprep DNA Method below).

Identification of Mutant Subclones and Sequence Verification. Minipreps were rapidly screened for the presence of B1 parental or mutant sequences by digestion with restriction enzymes for sites introduced by the mutagenic primers. Plasmids containing mutant restriction site markers were then sequenced across the Nsi I to stop codon region to verify the presence of desired mutations and absence of unplanned ones (see DNA Sequencing Method below).

Transposition and Isolation of Bacmid DNA. DH10Bac competent cells were thawed on ice, and 100 μL of cells were placed into 15 mL polypropylene tubes. 5 μL (approximately 1 ng) of the pFastBac1-ATIII transfer plasmid miniprep DNA was added to the cells and gently mixed. The mixture was placed on ice for 30 minutes. The mixture was heat shocked at 42° C. for 45 seconds and then chilled for 2 minutes. 900 μL of S.O.C medium was added to the mixture and the sample was rotated for 4 hours at 37° C. Cells were serially diluted in S.O.C. medium 10-, 100, and 1000-fold, and 100 μL of each dilution was plated on Luria agar plates containing 50 μg/mL kanamycin, 7 μg/mL gentamicin, 10 μg/mL tetracycline, 300 μg/mL Bluo-Gal and 40 μg/mL IPTG. Plates were incubated at 37° C. for 36–48 hours.

White colonies, containing the recombinant bacmid resulting from Tn7 transposition of the polyhedrin/ATIII cassette and associated elimination of lac Z a-peptide expression, were picked and streaked onto fresh plates to verify the white phenotype. Then single white colonies were inoculated into 2 mL LB medium and grown overnight at 37° C. 1 mL of culture was transferred to microfuge tube and spun for 1 minute. The supernatant was discarded and the pellet was resuspended in 0.3 mL of Solution I (15 mM Tris-HCl, pH 8.0, 10 mM EDTA, 100 μg/mL RNase). 0.3 mL of Solution II (0.2 N NaOH, 1% SDS) was added and the sample was gently mixed prior to incubating at room temperature for 5 minutes. Following addition of 0.3 mL of 3 M KAc, pH 5.5, the sample was placed on ice for 5 to 10 minutes. The sample was next centrifuged for 10 minutes at 4C (12,000×g) and the supernatant was transferred to a clean microfuge tube containing 0.8 mL absolute isopropanol. Bacmid DNA was precipitated by inverting the tube several times and placing it on ice for 5 to 10 minutes. The sample was microfuged for 15 minutes, the supernatant was aspirated and 0.5 mL of 70% ethanol was added to the pellet. The tube was inverted several times and then microcentrifuged for 5 minutes. The supernatant was aspirated and the pellet was air-dried and resuspended in 40 μL TE. The recombinant bacmid DNA was then transfected into Sf9 cells to produce a primary virus stock.

Transfection of Sf9 cells and Harvest of Primary Virus Stock. Individual wells of 6-well tissue culture dishes were seeded with 1×106 Sf9 cells and incubated in a 27° C. humidified incubator for at least 1 hour. Solution A (5 μL miniprep bacmid DNA in 100 μL Sf-900 II medium) and Solution B (6 μL CELLFECTIN reagent (Gibco/BRL) in 100 μL Sf-900 II medium) were combined, gently mixed and incubated for 45 minutes at room temperature. 0.8 mL of Sf-900 II medium was added to the CELLFECTIN-DNA mixture. The medium was aspirated from the Sf9 cells. The cells were washed with 2 mL of Sf-900 II medium, then the 1 mL of CELLFECTIN-DNA mixture was applied to the cell monolayer. The cells were incubated for 5 hours at 27° C. The transfection mixture was aspirated and replaced with fresh Sf-900 II medium. The cells were incubated at 27° C. and the primary lysate virus stock was harvested 48 hours post-transfection.

Transformation

Competent E. coli INVaF' cells were removed from −70° C. storage and thawed on ice. 5 μL of ligation reaction or 5 ng of pUC18 control plasmid was added, and the sample was mixed gently before incubating on ice for 15 minutes. The cells were then heat shocked for 90 seconds at 45° C., followed by incubation on wet ice for 1 minute. 500 μL of sterile LB was added to each tube, and tubes were placed on Ferris wheel and regrown at 37° C. for 30–60 minutes during which time phenotypic expression of the drug resistance marker in transformed cells occurred. 300 μL of each experimental transformation reaction and 20 μL of the pUC18 control transformation were spread on LB agar plates containing ampicillin and X-gal. Plates were inverted and incubated overnight at 37° C. The transformation efficiency was calculated to be the product of 500 μL tunes the number of colonies divided by the product of the volume plated and amount of DNA added to the transformation control.

Miniprep DNA

This protocol was used to produce DNA for restriction enzyme analysis, sequencing, subcloning and transformations. An appropriate E. coli INVaF' colony was picked onto a master plate and then used to inoculate 5 mL LB-ampicillin. The culture tube was rotated overnight on a Ferris wheel at 37° C. The next day, the cells were pelleted for 10 min at 8000 rpm (SM-24 rotor) in a refrigerated Sorvall RC-5B centrifuge (6000×g), and the supernatant was discarded. 100 μL of Solution I (50 mM glucose, 10 mM EDTA, 25 mM Tris, pH 8.0 and 2 mg/mL freshly dissolved lysozyme) was added to the cell pellet, then the miniprep tube was vortexed and incubated at room temperature for 5 minutes. 200 μL of Solution II (0.2 N NaOH, 1% SDS) was added to each tube, and the rack of miniprep tubes was shaken back and forth several times before incubating at room temperature for 2 minutes. 150 μL of Solution III (3 M NaAc, pH 4.8) was added to each tube, and the rack of miniprep tubes was again shaken before transferring to −20° C. for at least 10 minutes. Miniprep tubes were removed from the freezer and immediately spun in a Sorvall-RC5B refrigerated centrifuge at 4C and 20,000×g for 15 min (15,000 rpm, SM-24 rotor). After the centrifugation, the tubes were kept cold in the rotor (to prevent solubilization of SDS upon sample warming) prior to removing 450 μL of the supernatant and adding it to 450 μL equilibrated phenol. After vortexing, 450 μL of chloroform was added and vortexed. The solution was then microcentrifuged for 3 minutes to separate the phases. 400 μL of the top aqueous phase was transferred to a clean microfuge tube and 900 μL of absolute ethanol was added. After mixing by inversion several times, the tube was microcentrifuged for 3 minutes. The ethanol was carefully aspirated, and 100 μL of Solution IV (0.3 M NaAc, pH 6.8) was added to the pellet. After vigorous vortexing, 900 μL of 80% ethanol was added, and then the sample was mixed by inversion and microcentrifuged for 3 minutes. The ethanol was again carefully aspirated, and the pellet was dried in a SpeedVac (Savant). Dried pellets were resuspended in 50 μL of RNase solution (200 μg/mL in water). 3 mL of miniprep DNA prepared in this way contained 500 ng-1 μg of plasmid DNA, which was sufficient for one gel lane.

DNA Sequencing

LEAI and Group I mutant miniprep DNAs were sequenced using a modified Sanger protocol (Sanger et al., 1977). All sequencing performed on variants generated using the pBlueBac2 transfer plasmid was done using Sequenase v2.0 and reagents from the USB Sequenase kit. 35S-dATP was purchased from Amershanm. The sequencing reactions were performed on 1 μL of linearized miniprep DNA (~300 ng double-stranded plasmid DNA), which was denatured with 0.5 pmoles of primer at 3. 1201F by heating at 95° C. for 3 minutes and annealing on ice. Labeling reactions contained 10 μL of the template-primer mixture, 1 μL of 100 mM DTT, 2 μL of 1:5 to 1:20 diluted dGTP labeling mix, 0.5 μL of 35S-dATP (10 mCi/mL, >1000 mCi/mol) and 2 μL of 8-fold diluted Sequenase v2.0 (13 units/mL), added last. The elongation reaction was incubated at room temperature for 2–4 minutes and then split into 4 aliquots which were terminated by adding ddNTPs to a final concentration of 1 μM. The sequencing reactions were analyzed on 5% "Long Ranger" acrylamide gels containing 1.2×TBE buffer and 7 M urea. The electrophoresis running buffer was 0.6×TBE. After electrophoresis, the gel was dried on 3MM Whatman paper using a BioRad gel drier. The dried gels were exposed to Fuji RX x-ray film (Fuji, Inc., Stanford, Conn.) for 5–7 days at −70° C.

Sequencing of Group II mutants was performed at the University of Utah DNA Sequencing Facility on an ABI 373 machine with fluorescent DNA chemistry.

Western Blotting

Reduced samples were electrophoresed on 12% SDS-Duracryl-polyacrylamide gels using the Mini-PROTEAN II electrophoresis cell (BioRad) at 200 volts for 75 minutes. Separated proteins were transferred to PVDF membranes (Immobilon-P, Millipore, Bedford, Mass.) using a PolyBlot Transfer System (Model SBD1000, American Bionetics, Hayward, Calif.). A low ionic strength, discontinuous buffer system consisting of Anode buffer no. 1 (0.3 M Tris, 20% methanol, pH 10.4), Anode buffer no. 2 (25 mM Tris, 20% methanol, pH 10.4) and Cathode buffer (25 mM Tris, 40 mM 6-aminohexanoic acid, 20% methanol, pH 9.4) was used for protein blotting. 3-½"×2-¼" blots were transferred at 125 mA for 20 minutes. Membranes were blocked with 5% non-fat dry milk (NFDM) in TBST for 30 minutes and then incubated with sheep anti-human-ATIII Ig (1:5000 in TBST with 5% NFDM) overnight at 4° C. After three washes with TBST, 10 minutes each, membranes were incubated at room temperature with alkaline phosphatase-conjugated donkey-anti-sheep Ig (1:3000 in TBST with 5% NFDM). After extensive washing with TBS, the blot was developed with 50 ml alkaline phosphatase buffer (100 mM NaCl, 5 mM MgCl2, 100 mM diethanolamine, pH 9.5) containing 16 mg/L 5-bromo-chloro-3-indolyl phosphate (XP) and 32 mg/L nitro blue tetrazolium (NBT) until adequate staining was obtained. Blots were washed with deionized water and air dried.

Small-Scale Baculovirus Stock Amplification 150 mL suspension cultures of logarithmic Sf9 cells in fresh Sf-900 II medium (1–2×106 cells/mL, >98% viability)

were infected with 20 μL of secondary lysate. Infected culture were incubated at 27° C., 150 rpm. At 3 days post infection, the supernatant was harvested. Fetal bovine serum was added to 10% to stabilize the virus stocks, which were then maintained at 4° C. or -70° C. for short and long term storage, respectively.

Large-Scale Expression of Recombinant ATIII Variants

Larger volumes (0.8–1.6 L) of recombinant ATIII were produced by infecting glass Erlenmeyer flasks of logarithmic Sf9 cells in Sf-900 II medium (1–2×106 cells/mL, >98% viability) with 0.5% (v/v) virus stock. Cultures were maintained at 27° C., 150 rpm. Conditioned media were harvested at 4 days post-infection and prepared for chromatography by adding sodium azide to 0.02% (w/v) and removing cells and particulate matter by low-speed centrifugation and passage through 0.45 micron cellulose acetate membranes (Zap Caps, Schleicher and Schuell).

Heparin Affinity Chromatography

Cleared supernatants of culture medium were pumped through two tandem 5 mL Econopak heparin cartridges at 0.4 mL/min. The column was washed with 150 mL buffer A (20 mM phosphate, pH 7.4, 100 mM NaCl, 0.1 mM EDTA) followed by 50 mL of buffer A with 0.5 M NaCl. Bound protein was eluted from the column with a 0.6–3.1 M NaCl gradient 1.5 mL fractions were collected into 4.5 mL of 1×PE. NaCl concentration of fractions were determined on a conductivity meter calibrated against 1 g/L NaCl. The presence and purity of ATIII in the gradient fractions was determined by SYPRO Red staining of aliquots resolved on 10% polyacrylamide Laemmli gels. Peak fractions were pooled and dialyzed.

Dialysis

Pooled ATIII fractions were placed in Spectropor 2 dialysis tubing (12,000–14,000 MWCO) and dialyzed against at least three 1000-fold volumes of PNE buffer at 4° C. Dialyzed proteins were then concentrated using 30,000 MWCO Vivaspin 15 tangential flow concentrators (Vivascience LTD, Binbrook, England) as per manufacturer's instructions. Concentrators were prespun with PNE-PEG to decrease protein adsorption. Concentrated preparations were then microfuged for 5 minutes at 4° C. to remove particulates and aggregates, and the samples were aliquoted into 0.5–1.0 mL volumes and stored at -70° C.

Example 3

Analysis of Modified ATIIIs

Determination of Thrombin and Factor Xa Second-Order Rate Constants

Progressive second order rate constants of association (kapp) for thrombin and factor Xa with antithrombin III variants were determined under pseudo-first conditions (where inhibitor concentration greatly exceeds enzyme concentration). Forty μL aliquots of ATIII samples at varying concentrations (450 nM, 300 nM, 150 nM) in PNE-PEG plus 50 μg/mL polybrene (to neutralize any contaminating heparin) were preloaded into quadruplicate wells of a low-binding 96-well assay plate (Corning). The plate was maintained at 25° C., and 20 μL aliquots of 30 nM human thrombin or 15 nM human factor Xa were added to each of the four wells at successive 5 minute intervals. Reactions were quenched 5 minutes after addition of enzyme to the last of the wells by the adding 100 μL of 1.5 mM chromogenic substrate (S-2238 for thrombin; S-2765 for factor Xa). Residual enzyme activity was measured on a BioTek ELS11X kinetic plate reader controlled by a Macintosh SE with Deltasoft software. Initial rates of chromogenic substrate cleavage were monitored at 405 nm. The observed pseudo-first-order rate constant, kobs, was calculated from the negative slope of a plot of ln (residual enzyme activity) vs. time of enzyme and inhibitor co-incubation. Plots were generated using Kaleidagraph software. kapp was calculated by dividing the observed pseudo-first-order rate constant, kobs, by the inhibitor concentration.

Determination of ATIII Variant Sensitivity to Neutrophil Proteinases

ATIII variant sensitivity to inactivation by neutrophil proteinases were determined by monitoring the kinetics of inhibitor cleavage. Standard reaction conditions were: 1 μM ATII, 10 nM HNE or 50 nM cathepsin G, 50 μg/mL unfractionated heparin in PNE-PEG. The reaction volume was 150 μL. The protease was added last and the reaction mix was incubated at 37° C. At varying time points, 10 μL aliquots (corresponding to 500 ng of ATIII) were subsampled into non-reducing SDS sample buffer and quick-frozen in dry ice/ethanol. Samples were boiled prior to electrophoresis on 12% Duracryl polyacrylamide gels. Photographed gels were scanned and densitometrically analyzed as previously described. Percent residual native (uncleaved) ATIII was plotted vs. time of reaction to determine the half-lives of the variants.

Sensitivity of ATIII and Variants to Neutrophil Supernatants

Neutrophil supernatants were kindly prepared by Dr. Theodore Liou (University of Utah, Salt Lake City, Utah). 60 mL of freshly drawn citrated whole blood was diluted 1:1 with Hepes buffered saline (150 mM NaCl, 10 mM Hepes, pH 7.4). 30 mL of diluted whole blood was carefully layered over 20 mL Histopaque-1077 in a 50-mL conical polypropylene tube. The tube was centrifuged for 30 minutes at 850×g at room temperature. The Histopaque was carefully aspirated and discarded while being careful not to disturb the buffy coat layer. 20 mL of 2.5% Dextran in Hepes buffered saline was added to tube and the contents were mixed by inverting the tube several times. The tube was allowed to sit at room temperature for 20 minutes, during which time red cells aggregated and settled. The top, neutrophil-rich layer was aspirated, and the red cells were discarded. The neutrophil-rich layer was brought up to 50 mL with Hepes buffered saline in a new 50-mL tube and centrifuged at 475×g at room temperature for 10 minutes. The supernanant was removed, and the pellet was resuspended in 50 mL cold lysing solution (150 mM KH4Cl, 10 mM KHCO3, 1 mM EDTA, pH 7.2). The cells remained in lysing solution on ice for 3–5 minutes, and were then centrifuged at 475×g for 10 minutes at 4° C. The supernatant was discarded, and the cells resuspended in fresh Hank's buffered saline solution, pH 7.4 (HBSS) using a sterile disposable pipette. They were washed once more in HBSS and finally resuspended at a concentration of 3×107 PMN/mL.

Activating surfaces were prepared using 1" diameter sterile polystyrene culture dishes which were incubated with 75 μg of fibronectin (FN) in 1 mL HBSS for 1 hour. After rinsing three times with HBSS, plates were incubated with 800 μL of 1:16 goat anti-human FN IgG (Sigma F1509, lot 094H8868) or buffer for 1 hour, and again rinsed with HBSS three times. Supernatants were generated by adding 20–30× 106 PMN in 1 mL HBSS to each dish.

Supernatants from control and IgG stimulated neutrophils were assayed using the chromogenic substrates, MeO-Suc-Ala-Ala-Pro-Val-pNA (AAPV) and Suc-Ala-Ala-Pro-Phe-pNA (AAPF). Sixty μL aliquots of the supernatants were loaded into quadruplicate wells of a microplate. The plate was also loaded with standard curves for neutrophil elastase (20 nM, 4 nM, 0.8 nM, 0.16 nM and 0.32 nM) and cathepsin G (100 nM, 20 nM, 4 nM and 0.8 nM), and buffer controls. 100 μL of 0.66 mM AAPV was added to two wells of each quadruplicate set, and 100 μL of 0.66 mM AAPF was added to the other two wells. Substrate hydrolysis was measured in kinetic mode at 405 nm. The content of proteinase activity for each supernatant was estimated from the purified proteinase standards. Resistance of variants to inactivation by the neutrophil supernatant was performed using the standard reaction conditions described for the purified proteinases, substituting undiluted supernatant for purified proteinase.

Example 4

Properties of Modified ATIIIs

Properties of modified antithrombin Ms are summa in Table 3. Compared to plasma ATIII, which is sensitive to cleavage and inactivation by neutrophil elastase, the variants exhibited increased resistance to HNE, with prolongation of half-lives ranging from 4-fold to greater than 800-fold. Most of the modified ATMs retain the ability to inhibit factor Xa, and for 5 in this group, the rate of factor Xa inactivation more than doubled. Many of the modified ATIIIs retain the ability to inhibit thrombin. Several variants were tested for neutrophil resistance and resistance to cathepsin G. The degree of resistance to inactivation by supernatants of IgG activated human neutrophils and in the presence of activated neutrophils paralleled that determined in assays using purified HNE, and appeared to be independent of acquired cathepsin G sensitivity in the case of the Bb mutant.

Table 3 describes the results obtained from the experiments conducted according to the protocols described herein.

e Half-lives of inactivation by cathepsin G. Reaction conditions were 1 μM ATIII variant, 50 nM purified cathepsin G, 50 μg/mL unfractionated heparin, 20 mM NaPi, 100 mM NaCl, 100 _M EDTA, 0.1% polyethylene glycol 6000, pH 7.4, 37° C. Following exposure of ATIII variants to cathepsin G for different periods of time, native and cleaved ATIII molecules were separated by non-reducing SDS-polyacrylamide gel electrophoresis. SYPRO Red stained gels were photographed and scanned, and half-lives determined from plots of percent residual native ATIII vs. incubation time. $T_{1/2}$ are represented as Mean ±S.D.

f Half-lives of inactivation by supernatants of IgG activated human neutrophils. 1 μM recombinant ATIIIs were exposed to supernatants from IgG-stimulated neutrophils (ca. 2 nM of elastase activity equivalents) in the presence of 50 μg/mL heparin. Reactions were stopped at different times and analyzed by SDS-PAGE as described in d and e.

g Apparent second-order rate constants for thrombin inhibition. Assays were run under pseudo-first order conditions and contained ATIIIs (300 nM, 200 nM or 100 nM), 10 nM thrombin, 20 mM NaPi, 100 mM NaCl, 100 μM EDTA, 0.1% polyethylene glycol 6000, 50 μg/mL polybrene, pH 7.4, 25° C. Reactions were quenched and

TABLE 3

| Variant | Sequence[a] P9 8 7 6 5 4 3 2 1[b] A B C D E F[c] | HNE resistance[d] $T_{1/2}$, min | Cathepsin G resistance[e] $T_{1/2}$, min | Neutrophil resistance[f] $T_{1/2}$, min | Thrombin inhibition[g] $k_{app}$, ×10³ M⁻¹s⁻¹ | Factor Xa inhibition[h] $k_{app}$, ×10³ M⁻¹s⁻¹ | SEQ ID |
|---|---|---|---|---|---|---|---|
| Plasma AT | S T A V V I A G R | <0.5 | | | 4.9 | 1.6 | |
| N135A | S T A V V I A G R | 0.7 ± 0.1 | 18.2 ± 4.4 | 1.25 | 3.7 ± 0.8 | 2.9 ± 0.6 | |
| LEAI | S T A L E A I G R | 2.8 ± 0.9 | 6.1 | | 3.6 ± 0.3 | 7.0 ± 0.7 | 1 |
| 7EVEA | S T E V E A A G R | 5.6 ± 0.2 | | | 0.6 ± 0.1 | 4.8 ± 0.4 | 2 |
| 5EA | S T A V E A A G R | 3.2 | | | 0.6 | 3.1 | 3 |
| Bb | S T E G F F S G R | 15.8 ± 2.6 | 1.4 ± 0.3 | 30 | 3.6 ± 0.4 | 4.5 ± 0.6 | 4 |
| Bb.A | S T E G E A S G R | 27.4 ± 1.5 | R (>45) | R (>45) | 0.5 ± 0.1 | 6.2 ± 0.3 | 5 |
| Bb.B | S T E G E G S G R | 44.8 ± 0.3 | 16.2 | | NR[1] | 0.7 ± 0.2 | 6 |
| Bb.C | S E E G E A S G R | 437 ± 0.5 | | | 0.4 ± 0.5 | 0.2 ± 0.2 | 7 |
| Bb.D | S E E G E G S G R | R[1] (>45) | | | 0.1 | NR | 8 |
| 13.A | S T A V E G A G R | 2.1 ± 1.7 | | | 0.2 ± 0.3 | 0.5 ± 0.2 | 9 |
| 13.B | S T E V E G A G R | 7.6 | | | NR | 2.8 | 10 |
| 13.C | S T E L E G A G R | 10.1 | | | NR | 5.1 | 11 |
| 13.D | S T A L E G A G R | 2.6 | | | NR | 3.3 | 12 |
| Aa | S T A E G G G G R | 9.1 ± 1.3 | | | 0.4 ± 0.1 | 0.4 ± 0.4 | 13 |
| F2A' | S T O T P P N G R | 2.6 | | | 1.6 ± 0.4 | 3.6 ± 0.9 | 14 |
| FF | S T A V F F A G R | <2.5 | | | 1.4 | 3.0 | 15 |

Footnotes to Table 3.
a Substituted amino acids are underlined.
b Numbering of residues amino terminal to scissile P1–P1' bond of proteinase substrates and inhibitors according to the convention of Schechter and Berger (Biochem Biophys. Res. Commn., 27:157–162, 1967). The P1 residue of human antithrombin III is arginine-393.
c Code used in formulae of claims. A=residue 386=P8; B=residue 387=P7; C=residue 388=P6; D=residue 389= P5; E-=residue 390=P4; F=residue 391=P3
d Half-lives of inactivation by neutrophil elastase. Reaction conditions were 1 μM ATIII variant, 10 nM purified human neutrophil elastase (HNE), 50 μg/mL unfractionated heparin, 20 mM NaPi, 100 mM NaCl, 100 μM EDTA, 0.1% polyethylene glycol 6000, pH 7.4, 37° C. Following exposure of ATIII variants to HNE for different periods of time, native and cleaved ATIII molecules were separated by non-reducing SDS-polyacrylamide gel electrophoresis. SYPRO Red stained gels were photographed and scanned, and half-lives determined from plots of percent residual native ATIII vs. incubation time. $T_{1/2}$ are represented as Mean ±S.D.

residual enzyme activity was determined with S-2238. Initial rates of substrate cleavage were monitored at 405 nm on a kinetic plate reader. $k_{obs}$ was calculated from the negative slope of a plot of ln (residual enzyme activity) vs. time of enzyme and inhibitor co-incubation. $k_{app}=k_{obs}/$ [I]. Values represented as Mean±S.D.

h Apparent second-order rate constants for factor Xa inhibition. Assays were run under pseudo-first order conditions and contained ATIIIs (300 nM, 200 nM or 100 nM), 5 nM factor Xa, 20 mM NaPi, 100 mM NaCl, 100 μM EDTA, 0.1% polyethylene glycol 6000, 50 μg/mL polybrene, pH 7.4, 25° C. Reactions were quenched and residual enzyme activity was determined with S-2765. Initial rates of substrate cleavage were monitored at 405 nm on a kinetic plate reader. kobs, was calculated from the negative slope of a plot of in (residual enzyme activity) vs. time of enzyme and inhibitor co-incubation. kapp= kobs/[I].

i R—Resistant to cleavage up to longest time point tested (indicated in parentheses).
j NR—nonreactive

What is claimed is:

1. An elastase-resistant antithrombin III (ATIII) comprising at least two modifications, wherein the modifications occur at positions P4 and P5 of the ATIII, wherein P4 and P5 are the fourth and fifth amino acids towards the amino terminal side of the scissile bond of the reactive center respectively, wherein P4 comprises an amino acid selected from the group consisting of alanine; phenylalanine; glycine; and proline, and wherein P5 comprises an amino acid selected from the group consisting of glutamic acid; phenylalanine; glycine; and proline wherein the elastase-resistant ATIII has greater resistance to human neutrophil elastase as compared to plasma ATIII wherein the ATIII retains a thrombin inhibitory activity defined by a $k_{app}$ of at least about $0.2M^{-1}\ sec^{-1}\times 10^3$.

2. The elastase-resistant ATIII of claim 1, wherein the ATIII further comprises three additional modifications, wherein the modifications occur at positions P6, P7, and P8 of the ATIII, wherein P6, P7, and P8 are the sixth, seventh, and eighth amino acids towards the amino terminal side of the scissile bond of the reactive center respectively, wherein P8 is glutamic acid, wherein residue P7 comprises an amino acid selected from the group consisting of glutamic acid and glutamine, and wherein P6 comprises an amino acid selected from the group consisting of: leucine; glycine; glutamic acid; and threonine.

3. The elastase-resistant ATIII of claim 1, wherein the ATIII further comprises one additional modification, wherein the modification occurs at position P3 of the ATIII, wherein P3 is the third amino acid towards the amino terminal side of the scissile bond of the reactive center, and wherein P3 comprises an amino acid selected from the group consisting of isoleucine; serine; glycine; and asparagine.

4. The ATIII of claim 1, wherein the ATIII is in a pharmaceutically acceptable formulation.

5. The elastase-resistant ATIII of claim 1, wherein the ATIII has enhanced heparin binding activity.

6. The ATIII of claim 5, wherein the ATIII is in a pharmaceutically acceptable formulation.

7. The elastase-resistant ATIII of claim 1, wherein the ATIII has enhanced heparin binding activity, and wherein the ATIII has a mutation two residues subsequent to a glycosylation site.

8. The ATIII of claim 7, wherein the ATIII is in a pharmaceutically acceptable formulation.

9. The ATIII of claim 7, wherein the glycosylation site occurs at position 135 of SEQ ID NO:35.

10. The ATIII of claim 7, wherein the glycosylation site occurs at position 192 of SEQ ID NO:35.

11. The ATIII of claim 1, wherein the ATIII has enhanced heparin binding activity, and wherein the ATIII has a mutation at position 96, 135, 155, or 192 of SEQ ID NO:35.

12. An elastase-resistant antithrombin III (ATIII) comprising at least three modifications, wherein the modifications occur at positions P4, P5, and P6 of the ATIII, wherein P4, P5, and P6 are the fourth, fifth, and sixth amino acids towards the amino terminal side of the scissile bond of the reactive center respectively, wherein P4 comprises an amino acid selected from the group consisting of alanine; phenylalanine; glycine; and proline, wherein P5 comprises an amino acid selected from the group consisting of glutamic acid; phenylalanine; glycine; and proline, and wherein P6 comprises an amino acid selected from the group consisting of leucine, glycine, glutamic acid, and threonine, wherein the elastase-resistant ATIII has greater resistance to human neutrophil elastase as compared to plasma ATIII wherein the ATIII retains a thrombin inhibitory activity defined by a $k_{app}$ of at least about $0.2M^{-1}S^{-1}\times 10^3$.

13. The elastase-resistant ATIII of claim 12, wherein P6 is glycine.

14. The elastase-resistant ATIII of claim 13, wherein P5 is phenylalanine or glutamic acid.

15. An elastase-resistant antithrombin III (ATIII) comprising at least two modifications, wherein the modifications occur at positions P3 and P6 of the ATIII, wherein P3 and P6 are the third and sixth amino acids towards the amino terminal side of the scissile bond of the reactive center respectively, wherein P3 comprises an amino acid selected from the group consisting of isoleucine; serine; glycine; and asparagine, and wherein P6 comprises an amino acid selected from the group consisting of leucine; glycine; glutamic acid; and threonine, wherein the elastase-resistant ATIII has greater resistance to human neutrophil elastase as compared to plasma ATIII wherein the ATIII retains a thrombin inhibitory activity defined by a $k_{app}$ of at least about $0.2M^{-1}S^{-1}\times 10^3$.

16. The elastase-resistant ATIII of claim 15, wherein P3 is serine.

17. The elastase-resistant ATIII of claim 15, wherein P6 is glycine.

18. The elastase-resistant AIII of claim 17, wherein P3 is serine.

19. An elastase-resistant antithrombin III (ATIII) comprising at least three modifications, wherein the modifications occur at positions P3, P6, and P7 of the ATIII, wherein P3, P6, and P7 are the third, sixth, and seventh amino acids towards the amino terminal side of the scissile bond of the reactive center respectively, wherein P3 comprises an amino acid selected from the group consisting of isoleucine; serine; glycine; and asparagine, wherein P6 comprises an amino acid selected from the group consisting of leucine; glycine; glutamic acid; and threonine, and wherein P7 comprises an amino acid selected from the group consisting of glutamic acid and glutamine, wherein the elastase-resistant ATIII has greater resistance to human neutrophil elastase as compared to plasma ATIII wherein the ATIII retains a thrombin inhibitory activity defined by a $k_{app}$ of at least about $0.2M^{-1}S^{-1} \times 10^3$.

20. The elastase-resistant ATIII of claim 19, wherein P7 is glutamic acid.

21. The elastase-resistant ATIII of claim 20, wherein P3 is serine, and wherein P6 is glycine.

22. An elastase-resistant antithrombin III (ATIII) comprising at least five amino acid modifications, wherein the modifications occur at positions P3, P4, P5, P6, and P7 of the ATIII, wherein P3, P4, P5, P6, and P7 are the third, fourth, fifth, sixth, and seventh amino acids towards the amino terminal side of the scissile bond of the reactive center respectively, wherein P3 is serine, wherein P4 is phenylalanine, wherein P5 is phenylalanine, wherein P6 is glycine, and wherein P7 is glutamic acid, wherein the resistant-resistant ATIII has greater resistance to human neutrophil lactase as compared to plasma ATIII wherein the ATIII retains an antithrombin activity defined by a $k_{app}$ of at least about $0.2M^{-1}S^{-1} \times 10^3$.

23. An elastase-resistant antithrombin III (ATIII) comprising at least five amino acid modifications, wherein the modifications occur at positions P3, P4, P5, P6, and P7 of the ATIII, wherein P3, P4, P5, P6, and P7 are the third, fourth, fifth, sixth, and seventh amino acids towards the amino terminal side of the scissile bond of the reactive center respectively, wherein P3 is serine, wherein P4 is alanine, wherein P5 is glutamic acid, wherein P6 is glycine, and wherein P7 is glutamic acid, wherein the elastase-resistant ATIII has greater resistance to human neutrophil elastase as compared to plasma ATIII wherein the ATIII retains a thrombin inhibitory activity defined by a $k_{app}$ of at least about $0.2M^{-1}S^{-1} \times 10^3$.

24. An elastase-resistant antithrombin III wherein the amino acid sequence of residues 387–391 according to SEQ ID NO:35 is substituted with the amino acid sequence of residues 3 through 7 of SEQ ID NO:4, wherein the elastase-resistant ATIII has greater resistance to human neutrophil elastase as compared to plasma ATIII.

25. An resistant-resistant antithrombin III wherein the amino acid sequence of residues 387–391 according to SEQ ID NO:35 is substituted with the amino acid sequence of residues 3 through 7 of SEQ ID NO:5, wherein the resistant-resistant ATIII has greater resistance to human neutrophil lactase as compared to plasma ATIII.

26. An elastase-resistant antithrombin III (ATIII) comprising at least two modifications, wherein the modifications occur at positions P4 and P5 of the ATIII, wherein P4 and P5 are the fourth and fifth amino acids towards the amino terminal side of the scissile bond of the reactive center respectively, wherein P4 comprises an amino acid selected from the group consisting of alanine; glycine; and proline, and wherein P5 comprises an amino acid selected from the group consisting of glutamic acid; glycine; and proline, wherein the elastase-resistant ATIII has greater resistance to human neutrophil elastase as compared to plasma ATIII wherein the ATIII retains a thrombin inhibitory activity defined by a $k_{app}$ of at least about $0.2M^{-1}S^{-1} \times 10^3$.

27. An elastase-resistant antithrombin III (ATIII) comprising at least three modifications, wherein the modifications occur at positions P4, P5, and P6 of the ATIII, wherein P4, P5, and P6 are the fourth, fifth, and sixth amino acids towards the amino terminal side of the scissile bond of the reactive center respectively, wherein P4 is alanine, wherein P5 is glutamic acid; and wherein P6 is leucine, wherein the elastase-resistant ATIII has greater resistance to human neutrophil elastase as compared to plasma ATIII wherein the ATIII retains a thrombin inhibitory activity defined by a $k_{app}$ of at least about $0.2M^{-1}S^{-1} \times 10^3$.

28. An elastase-resistant antithrombin III (ATIII) comprising at least four modifications, wherein the modifications occur at positions P3, P4, P5, and P6 of the ATIII, wherein P3, P4, P5, and P6 are the third, fourth, fifth, and sixth amino acids towards the amino terminal side of the scissile bond of the reactive center respectively, wherein P3 is isoleucine, wherein P4 is alanine, wherein P5 is glutamic acid; and wherein P6 is leucine, wherein the elastase-resistant ATIII has greater resistance to human neutrophil elastase as compared to plasma ATIII wherein the ATIII retains a thrombin inhibitory activity defined by a $k_{app}$ of at least about $0.2M^{-1}S^{-1} \times 10^3$.

29. An elastase-resistant antithrombin III (ATIII) comprising at least two modifications, wherein the modifications occur at positions P4 and P6 of the ATIII, wherein P4 and P6 are the fourth and sixth amino acids towards the amino terminal side of the scissile bond of the reactive center respectively, wherein P4 comprises an amino acid selected from the group consisting of alanine; phenylalanine; glycine; and proline, and wherein P6 comprises an amino acid selected from the group consisting of leucine; glycine; glutamic acid; and threonine, wherein the resistant-resistant ATIII has greater resistance to human neutrophil elastase as compared to plasma ATIII wherein the ATIII retains a thrombin inhibitory activity defined by a $k_{app}$ of at least about $0.2M^{-1}S^{-1} \times 10^3$.

30. The ATIII of claim 29, wherein the P4 is alanine and P6 is leucine.

31. The elastase-resistant ATIII of claim 30, wherein the ATIII has enhanced heparin binding activity, and wherein the ATIII has a mutation two residues subsequent to a glycosylation site.

32. The ATIII of claim 31, wherein the ATIII is in a pharmaceutically acceptable formulation.

33. The ATIII of claim 31, wherein the glycosylation site occurs at position 135 of SEQ ID NO:35.

34. The ATIII of claim 31, wherein the glycosylation site occurs at position 192 of SEQ ID NO:35.

35. The ATIII of claim 29, wherein the ATIII has enhanced heparin binding activity, and wherein the ATIII has a mutation at position 96, 135, 155, or 192 of SEQ ID NO:35.

36. An elastase-resistant antithrombin III (ATIII) comprising four modifications, wherein the modifications occur at positions P3, P4, P5, and P6 of the ATIII, wherein P3, P4, P5, and P6 are the third, fourth, fifth, and sixth amino acids towards the amino terminal side of the scissile bond of the reactive center respectively, wherein P3 is isoleucine, wherein P4 alanine, wherein P5 is glutamic acid; and wherein P6 is leucine, wherein the elastase-resistant ATIII has greater resistance to human neutrophil elastase as compared to plasma ATIII wherein the ATIII retains a thrombin inhibitory activity defined by a $k_{app}$ of at least about $0.2M^{-1}S^{-1} \times 10^3$.

37. An elastase-resistant antithrombin III (ATIII) comprising at least two modifications, wherein the modifications occur at positions P4 and P5 of the ATIII, wherein P4 and P5 are the fourth and fifth amino acids towards the amino terminal side of the scissile bond of the reactive center respectively, wherein P4 comprises an amino acid selected from the group consisting of alanine; phenylalanine; glycine; and proline, and wherein P5 comprises an amino acid selected from the group consisting of glutamic acid; phenylalanine; glycine; and proline, wherein the elastase-resistant ATIII has greater resistance to human neutrophil elastase as compared to plasma ATIII wherein the ATIII retains a factor Xa inhibitory activity defined by a $k_{app}$ of at least about $0.2M^{-1}S^{-1} \times 10^3$.

38. The elastase-resistant ATIII of claim 37, wherein the ATIII further comprises three additional modifications, wherein the modifications occur at positions P6, P7, and P8 of the ATIII, wherein P6, P7, and P8 are the sixth, seventh, and eighth amino acids towards the amino terminal side of the scissile bond of the reactive center respectively, wherein P8 is glutamic acid, wherein residue P7 comprises an amino acid selected from the group consisting of glutamic acid and glutamine, and wherein P6 comprises an amino acid selected from the group consisting of: leucine; glycine; glutamic acid; and threonine.

39. The elastase-resistant ATIII of claim 37 wherein the ATIII further comprises one additional modification, wherein the modification occurs at position P3 of the ATIII, wherein P3 is the third amino acid towards the amino terminal side of the scissile bond of the reactive center, and wherein P3 comprises an amino acid selected from the group consisting of isoleucine; serine; glycine; and asparagine.

40. The ATIII of claim 37, wherein the ATIII is in a pharmaceutically acceptable formulation.

41. The elastase-resistant ATIII of claim 37, wherein the ATIII has enhanced heparin binding activity.

42. The ATIII of claim 41, wherein the ATIII is in a pharmaceutically acceptable formulation.

43. The elastase-resistant ATIII of claim 37, wherein the ATIII has enhanced heparin binding activity, and wherein the ATIII has a mutation two residues subsequent to a glycosylation site.

44. The ATIII of claim 43, wherein the glycosylation site occurs at position 135 of SEQ ID NO:35.

45. The ATIII of claim 43, wherein the glycosylation site occurs at position 192 of SEQ ID NO:35.

46. The ATIII of claim 37, wherein the ATIII has enhanced heparin binding activity, and wherein the ATIII has a mutation at position 96, 135, 155, or 192 of SEQ ID NO:35.

47. An elastase-resistant antithrombin III (ATIII) comprising at least three modifications, wherein the modifications occur at positions P4, P5, and P6 of the ATIII, wherein P4, P5, and P6 are the fourth, fifth, and sixth amino acids towards the amino terminal side of the scissile bond of the reactive center respectively, wherein P4 comprises an amino acid selected from the group consisting of alanine; phenylalanine; glycine; and proline, wherein P5 comprises an amino acid selected from the group consisting of glutamic acid; phenylalanine; glycine; and proline, and wherein P6 comprises an amino acid selected from the group consisting of leucine, glycine, glutamic acid, and threonine, wherein the elastase-resistant ATIII has greater resistance to human neutrophil elastase as compared to plasma ATIII wherein the ATIII retains a factor Xa inhibitory activity defined by a $k_{app}$ of at least about $0.2M^{-1}S^{-1}10^3$.

48. The elastase-resistant ATIII of claim 47, wherein P6 is glycine.

49. The elastase-resistant ATIII of claim 48, wherein P5 is phenylalanine or glutamic acid.

50. An elastase-resistant antithrombin III (ATIII) comprising at least two modifications, wherein the modifications occur at positions P3 and P6 of the ATIII, wherein P3 and P6 are the third and sixth amino acids towards the amino terminal side of the scissile bond of the reactive center respectively, wherein P3 comprises an amino acid selected from the group consisting of isoleucine; serine; glycine; and asparagine, and wherein P6 comprises an amino acid selected from the group consisting of leucine; glycine; glutamic acid; and threonine, wherein the elastase-resistant ATIII has greater resistance to human neutrophil elastase as compared to plasma ATIII wherein the ATIII retains a factor Xa inhibitory activity defined by a $k_{app}$ of at least about $0.2M^{-1}S^{-1} \times 10^3$.

51. The elastase-resistant ATIII of claim 50, wherein P3 is serine.

52. The elastase-resistant ATIII of claim 50, wherein P6 is glycine.

53. The elastase-resistant ATIII of claim 52, wherein P3 is serine.

54. An elastase-resistant antithrombin III (ATIII) comprising at least three modifications, wherein the modifications occur at positions P3, P6, and P7 of the ATIII, wherein P3, P6, and P7 are the third, sixth, and seventh amino acids towards the amino terminal side of the scissile bond of the reactive center respectively, wherein P3 comprises an amino acid selected from the group consisting of isoleucine; serine; glycine; and asparagine, wherein P6 comprises an amino acid selected from the group consisting of leucine; glycine; glutamic acid; and threonine, and wherein P7 comprises an amino acid selected from the group consisting of glutamic acid and glutamine, wherein the elastase-resistant ATIII has greater resistance to human neutrophil elastase as compared to plasma ATIII wherein the ATIII retains a factor Xa inhibitory activity defined by a $k_{app}$ of at least about $0.2M^{-1}S^{-1} \times 10^3$.

55. The elastase-resistant ATIII of claim 54, wherein P7 is glutamic acid.

56. The elastase-resistant ATIII of claim 55, wherein P3 is serine, and wherein P6 is glycine.

57. An elastase-resistant antithrombin III (ATIII) comprising at least five amino acid modifications, wherein the modifications occur at positions P3, P4, P5, P6, and P7 of the ATIII, wherein P3, P4, P5, P6, and P7 are the third, fourth, fifth, sixth, and seventh amino acids towards the amino terminal side of the scissile bond of the reactive center respectively, wherein P3 is serine, wherein P4 is phenylalanine, wherein P5 is phenylalanine, wherein P6 is glycine, and wherein P7 is glutamic acid, wherein the elastase-resistant ATIII has greater resistance to human neutrophil elastase as compared to plasma ATIII wherein the ATIII retains a factor Xa inhibitory activity defined by a $k_{app}$ of at least about $0.2M^{-1}S^{-1} \times 10^{3-}$.

58. An elastase-resistant antithrombin III (ATIII) comprising at least five amino acid modifications, wherein the modifications occur at positions P3, P4, P5, P6, and P7 of the ATIII, wherein P3, P4, P5, P6, and P7 are the third, fourth, fifth, sixth, and seventh amino acids towards the amino terminal side of the scissile bond of the reactive center respectively, wherein P3 is serine, wherein P4 is alanine, wherein P5 is glutamic acid, wherein P6 is glycine, and wherein P7 is glutamic acid, wherein the elastase-resistant ATIII has greater resistance to human neutrophil elastase as compared to plasma ATIII wherein the ATIII retains a factor Xa inhibitory activity defined by a $k_{app}$ of at least about $0.2M^{-1}S^{-1} \times 10^3$.

59. An elastase-resistant antithrombin III (ATIII) comprising at least two modifications, wherein the modifications occur at positions P4 and P5 of the ATIII, wherein P4 and P5 are the fourth and fifth amino acids towards the amino terminal side of the scissile bond of the reactive center respectively, wherein P4 comprises an amino acid selected from the group consisting of alanine; glycine; and proline, and wherein P5 comprises an amino acid selected from the group consisting of glutamic acid; glycine; and proline, wherein the elastase-resistant ATIII has greater resistance to human neutrophil elastase as compared to plasma ATIII wherein the ATIII retains a factor Xa inhibitory activity defined by a $k_{app}$ of at least about $0.2M^{-1}S^{-1} \times 10^3$.

60. An elastase-resistant antithrombin III (ATIII) comprising at least three modifications, wherein the modifications occur at positions P4, P5, and P6 of the ATIII, wherein P4, P5, and P6 are the fourth, fifth, and sixth amino acids towards the amino terminal side of the scissile bond of the reactive center respectively, wherein P4 is alanine, wherein P5 is glutamic acid; and wherein P6 is leucine, wherein the elastase-resistant ATIII has greater resistance to human neutrophil elastase as compared to plasma ATIII wherein the ATIII retains a factor Xa inhibitory activity defined by a $k_{app}$ of at least about $0.2M^{-1}S^{-1} \times 10^3$.

61. An elastase-resistant antithrombin III (ATIII) comprising at least four modifications, wherein the modifications occur at positions P3, P4, P5, and P6 of the ATIII, wherein P3, P4, P5, and P6 are the third, fourth, fifth, and sixth amino acids towards the amino terminal side of the scissile bond of the reactive center respectively, wherein P3 is isoleucine, wherein P4 is alanine, wherein P5 is glutamic acid; and wherein P6 is leucine, wherein the elastase-resistant ATIII has greater resistance to human neutrophil elastase as compared to plasma ATIII wherein the ATIII retains a factor Xa inhibitory activity defined by a $k_{app}$ of at least about $0.2M^{-1}S^{-1} \times 10^3$.

62. An elastase-resistant antithrombin III (ATIII) comprising at least two modifications, wherein the modifications occur at positions P4 and P6 of the ATIII, wherein P4 and P6 are the fourth and sixth amino acids towards the amino terminal side of the scissile bond of the reactive center respectively, wherein P4 comprises an amino acid selected from the group consisting of: alanine; phenylalanine; glycine; and proline, and wherein P6 comprises an amino acid selected from the group consisting of: leucine; glycine; glutamic acid; and threonine wherein the elastase-resistant ATIII has greater resistance to human neutrophil elastase as compared to plasma ATIII wherein the ATIII retains a factor Xa inhibitory activity defined by a $k_{app}$ of at least about $0.2M^{-1}S^{-1} \times 10^3$.

63. The ATIII of claim 62, wherein the P4 is alanine and P6 is leucine.

64. The elastase-resistant ATIII of claim 63, wherein the ATIII has enhanced heparin binding activity, and wherein the ATIII has a mutation two residues subsequent to a glycosylation site.

65. The ATIII of claim 64, wherein the ATIII is in a pharmaceutically acceptable formulation.

66. The ATIII of claim 64, wherein the glycosylation site occurs at position 135 of SEQ ID NO:35.

67. The ATIII of claim 64, wherein the glycosylation site occurs at position 155 of SEQ ID NO:35.

68. The ATIII of claim 62, wherein the ATIII has enhanced heparin binding activity, and wherein the ATIII has a mutation at position 96, 135, 155, or 192 of SEQ ID NO:35.

69. An elastase-resistant antithrombin III (ATIII) comprising four modifications, wherein the modifications occur at positions P3, P4, P5, and P6 of the ATIII, wherein P3, P4, P5, and P6 are the third, fourth, fifth, and sixth amino acids towards the amino terminal side of the scissile bond of the reactive center respectively, wherein P3 is isoleucine, wherein P4 alanine, wherein P5 is glutamic acid; and wherein P6 is leucine, wherein the elastase-resistant ATIII has greater resistance to human neutrophil elastase as compared to plasma ATIII wherein the ATIII retains a factor Xa inhibitory activity defined by a kapp of at least about $0.2M^{-1}S^{-1} \times 10^3$.

70. An elastase-resistant antithrombin m (ATIII) comprising at least two modifications, wherein the modifications occur at positions P4 and P5 of the ATIII, wherein P4 and P5 are the fourth and fifth amino acids towards the amino terminal side of the scissile bond of the reactive center respectively, wherein P4 comprises an amino acid selected from the group consisting of: alanine; phenylalanine; glycine; and proline, and wherein P5 comprises an amino acid selected from the group consisting of: glutamic acid; phenylalanine; glycine; and proline, wherein the elastase-resistant ATIII has greater resistance to human neutrophil elastase as compared to plasma ATIII wherein the ATIII retains a thrombin inhibitory activity which is at least about two percent of plasma ATIII thrombin inhibitory activity.

71. The ATIII of claim 70, wherein the ATIII is in a pharmaceutically acceptable formulation.

72. The elastase-resistant ATIII of claim 70 wherein the ATIII further comprises three additional modifications, wherein the modifications occur at positions P6, P7, and P8 of the ATIII, wherein P6, P7, and P8 are the sixth, seventh, and eighth amino acids towards the amino terminal side of the scissile bond of the reactive center respectively, wherein P8 is glutamic acid, wherein residue P7 comprises an amino acid selected from the group consisting of glutamic acid and glutamine, and wherein P6 comprises an amino acid selected from the group consisting of: leucine; glycine; glutamic acid; and threonine.

73. The elastase-resistant ATIII of claim 70, wherein the ATIII further comprises one additional modification, wherein the modification occurs at position P3 of the ATIII, wherein P3 is the third amino acid towards the amino terminal side of the scissile bond of the reactive center, and wherein P3 comprises an amino acid selected from the group consisting of isoleucine; serine; glycine; and asparagine.

74. The ATIII of claim 70, wherein the ATIII is in a pharmaceutically acceptable formulation.

75. The elastase-resistant ATIII of claim 70, wherein the ATIII has enhanced heparin binding activity.

76. The ATIII of claim 75, wherein the AIII is in a pharmaceutically acceptable formulation.

77. The elastase-resistant ATIII of claim 70, wherein the ATIII has enhanced heparin binding activity, and wherein the ATIII has a mutation two residues subsequent to a glycosylation site.

78. The ATIII of claim 77, wherein the ATIII is in a pharmaceutically acceptable formulation.

79. The ATIII of claim 77, wherein the glycosylation site occurs at position 135 of SEQ ID NO:35.

80. The ATIII of claim 77, wherein the glycosylation site occurs at position 192 of SEQ ID NO:35.

81. The ATIII of claim 70, wherein the ATIII has enhanced heparin binding activity, and wherein the ATIII has a mutation at position 96, 135, 155, or 192 of SEQ ID NO:35.

82. An elastase-resistant antithrombin III (ATIII) comprising four modifications, wherein the modifications occur at positions P3, P4, P5, and P6 of the ATIII, wherein P3, P4, P5, and P6 are the third, fourth, fifth, and sixth amino acids towards the amino terminal side of the scissile bond of the reactive center respectively, wherein P3 is isoleucine, wherein P4 alanine, wherein P5 is glutamic acid; and wherein P6 is leucine, wherein the elastase-resistant ATIII has greater resistance to human neutrophil elastase as compared to plasma ATIII wherein the ATIII retains a thrombin inhibitory activity which is at least about two percent of plasma ATIII thrombin inhibitory activity.

83. An elastase-resistant antithrombin III (ATIII) comprising at least three modifications, wherein the modifications occur at positions P4, P5, and P6 of the ATIII, wherein P4, P5, and P6 are the fourth, fifth, and sixth amino acids towards the amino terminal side of the scissile bond of the reactive center respectively, wherein P4 comprises an amino acid selected from the group consisting of: alanine; phenylalanine; glycine; and proline, wherein P5 comprises an amino acid selected from the group consisting of glutamic acid; phenylalanine; glycine; and proline, and wherein P6 comprises an amino acid selected from the group consisting of leucine, glycine, glutamic acid, and threonine, wherein the elastase-resistant ATIII has greater resistance to human neutrophil elastase as compared to plasma ATIII wherein the ATIII retains a thrombin inhibitory activity which is at least about two percent of plasma ATIII thrombin inhibitory activity.

84. The elastase-resistant ATIII of claim 83, wherein P6 is glycine.

85. The elastase-resistant ATIII of claim 84, wherein P5 is phenylalanine or glutamic acid.

86. An elastase-resistant antithrombin III (ATIII) comprising at least two modifications, wherein the modifications occur at positions P3 and P6 of the ATIII, wherein P3 and P6 are the third and sixth amino acids towards the amino terminal side of the scissile bond of the reactive center respectively, wherein P3 comprises an amino acid selected from the group consisting of isoleucine; serine; glycine; and asparagine, and wherein P6 comprises an amino acid selected from the group consisting of leucine; glycine; glutamic acid; and threonine, wherein the elastase-resistant ATIII has greater resistance to human neutrophil elastase as compared to plasma ATIII wherein the ATIII retains a thrombin inhibitory activity which is at least about two percent of plasma ATIII thrombin inhibitory activity.

87. The elastase-resistant ATIII of claim 86, wherein P3 is serine.

88. The elastase-resistant ATIII of claim 86, wherein P6 is glycine.

89. The elastase-resistant ATIII of claim 88, wherein P3 is serine.

90. An elastase-resistant antithrombin III (ATIII) comprising at least three modifications, wherein the modifications occur at positions P3, P6, and P7 of the ATIII, wherein P3, P6, and P7 are the third, sixth, and seventh amino acids towards the amino terminal side of the scissile bond of the reactive center respectively, wherein P3 comprises an amino acid selected from the group consisting of isoleucine; serine; glycine; and asparagine, wherein P6 comprises an amino acid selected from the group consisting of leucine; glycine; glutamic acid; and threonine, and wherein P7 comprises an amino acid selected from the group consisting of glutamic acid and glutamine, wherein the resistant-resistant ATIII has greater resistance to human neutrophil elastase as compared to plasma ATIII wherein the ATIII retains a thrombin inhibitory activity which is at least about two percent of plasma ATIII thrombin inhibitory activity.

91. The elastase-resistant ATIII of claim 90, wherein P7 is glutamic acid.

92. The elastase-resistant ATIII of claim 91, wherein P3 is serine, and wherein P6 is glycine.

93. An elastase-resistant antithrombin III (ATIII) comprising at least five amino acid modifications, wherein the modifications occur at positions P3, P4, P5, P6, and P7 of the ATIII, wherein P3, P4, P5, P6, and P7 are the third, fourth, fifth, sixth, and seventh amino acids towards the amino terminal side of the scissile bond of the reactive center respectively, wherein P3 is serine, wherein P4 is phenylalanine, wherein P5 is phenylalanine, wherein P6 is glycine, and wherein P7 is glutamic acid, wherein the elastase-resistant ATIII has greater resistance to human neutrophil elastase as compared to plasma ATIII wherein the ATIII retains a thrombin inhibitory activity which is at least about two percent of plasma ATIII thrombin inhibitory activity.

94. An elastase-resistant antithrombin III (ATIII) comprising at least five amino acid modifications, wherein the modifications occur at positions P3, P4, P5, P6, and P7 of the ATIII, wherein P3, P4, P5, P6, and P7 are the third, fourth, fifth, sixth, and seventh amino acids towards the amino terminal side of the scissile bond of the reactive center respectively, wherein P3 is serine, wherein P4 is alanine, wherein P5 is glutamic acid, wherein P6 is glycine, and wherein P7 is glutamic acid, wherein the elastase-resistant ATIII has greater resistance to human neutrophil elastase as compared to plasma ATIII wherein the ATIII retains a thrombin inhibitory activity which is at least about two percent of plasma ATIII thrombin inhibitory activity.

95. An elastase-resistant antithrombin III (ATIII) comprising at least two modifications, wherein the modifications occur at positions P4 and P5 of the ATIII, wherein P4 and P5 are the fourth and fifth amino acids towards the amino terminal side of the scissile bond of the reactive center respectively, wherein P4 comprises an amino acid selected from the group consisting of alanine; glycine; and proline, and wherein P5 comprises an amino acid selected from the group consisting of glutamic acid; glycine; and proline, wherein the elastase-resistant ATIII has greater resistance to human neutrophil elastase as compared to plasma ATIII wherein the ATIII retains a thrombin inhibitory activity which is at least about two percent of plasma ATIII thrombin inhibitory activity.

96. An elastase-resistant antithrombin III (ATIII) comprising at least three modifications, wherein the modifications occur at positions P4, P5, and P6 of the ATIII, wherein P4, P5, and P6 are the fourth, fifth, and sixth amino acids towards the amino terminal side of the scissile bond of the reactive center respectively, wherein P4 is alanine, wherein P5 is glutamic acid; and wherein P6 is leucine, wherein the elastase-resistant ATIII has greater resistance to human neutrophil elastase as compared to plasma ATIII wherein the ATIII retains a thrombin inhibitory activity which is at least about two percent of plasma ATIII thrombin inhibitory activity.

97. An elastase-resistant antithrombin III (ATIII) comprising at least four modifications, wherein the modifications occur at positions P3, P4, P5, and P6 of the ATIII, wherein P3, P4, P5, and P6 are the third, fourth, fifth, and sixth amino acids towards the amino terminal side of the scissile bond of the reactive center respectively, wherein P3 is isoleucine, wherein P4 is alanine, wherein P5is glutamic acid; and wherein P6 is leucine, wherein the resistant-resistant ATIII has greater resistance to human neutrophil elastase as compared to plasma ATIII wherein the ATIII retains a thrombin inhibitory activity which is at least about two percent of plasma ATIII thrombin inhibitory activity.

98. An elastase-resistant antithrombin III (ATIII) comprising at least two modifications, wherein the modifications occur at positions P4 and P6 of the ATIII, wherein P4 and P6 are the fourth and sixth amino acids towards the amino terminal side of the scissile bond of the reactive center respectively, wherein P4 comprises an amino acid selected from the group consisting of alanine; phenylalanine; glycine; and proline, and wherein P6 comprises an amino acid selected from the group consisting of leucine; glycine; glutamic acid; and threonine, wherein the elastase-resistant ATIII has greater resistance to human neutrophil elastase as compared to plasma ATIII wherein the ATIII retains a thrombin inhibitory activity which is at least about two percent of plasma ATIII thrombin inhibitory activity.

99. The ATIII of claim 98, wherein the P4 is alamine and P6 is leucine.

100. The elastase-resistant ATIII of claim 99, wherein the ATIII has enhanced heparin binding activity, and wherein the ATIII has a mutation two residues subsequent to a glycosylation site.

101. The ATIII of claim 100, wherein the ATIII is in a pharmaceutically acceptable formulation.

102. The ATIII of claim 100, wherein the glycosylation site occurs at position 135 of SEQ ID NO:35.

103. The ATIII of claim 100, wherein the glycosylation site occurs at position 155 of SEQ ID NO:35.

104. The ATIII of claim 98, wherein the ATIII has enhanced heparin binding activity, and wherein the ATIII has a mutation at position 96, 135, 155, or 192 of SEQ ID NO:35.

105. An elastase-resistant antithrombin III (ATIII) comprising at least two modifications, wherein the modifications occur at positions P4 and P5 of the ATIII, wherein P4 and P5 are the fourth and fifth amino acids towards the amino terminal side of the scissile bond of the reactive center respectively, wherein P4 comprises an amino acid selected from the group consisting of alanine; phenylalanine; glycine; and proline, and wherein P5 comprises an amino acid selected from the group consisting of glutamic acid; phenylalanine; glycine; and proline, wherein the elastase-resistant ATIII has greater resistance to human neutrophil elastase as compared to plasma ATIII wherein the ATIII retains a factor Xa inhibitory activity which is at least about 12.5 percent of plasma ATIII factor Xa inhibitory activity.

106. The elastase-resistant ATIII of claim 105 wherein the ATIII further comprises three additional modifications, wherein the modifications occur at positions P6, P7, and P8 of the ATIII, wherein P6, P7, and P8 are the sixth, seventh, and eighth amino acids towards the amino terminal side of the scissile bond of the reactive center respectively, wherein P8 is glutamic acid, wherein residue P7 comprises an amino acid selected from the group consisting of glutamic acid and glutamine, and wherein P6 comprises an amino acid selected from the group consisting of: leucine; glycine; glutamic acid; and threonine.

107. The elastase-resistant ATIII of claim 105 wherein the ATIII further comprises one additional modification, wherein the modification occurs at position P3 of the ATIII, wherein P3 is the third amino acid towards the amino terminal side of the scissile bond of the reactive center, and wherein P3 comprises an amino acid selected from the group consisting of isoleucine; serine; glycine; and asparagine.

108. The ATIII of claim 105, wherein the ATIII is in a pharmaceutically acceptable formulation.

109. The elastase-resistant ATIII of claim 105, wherein the ATIII has enhanced heparin binding activity.

110. The ATIII of claim 109, wherein the ATIII is in a pharmaceutically acceptable formulation.

111. The elastase-resistant ATIII of claim 105, wherein the ATIII has enhanced heparin binding activity, and wherein the ATIII has a mutation two residues subsequent to a glycosylation site.

112. The ATIII of claim 111, wherein the ATIII is in a pharmaceutically acceptable formulation.

113. The ATIII of claim 111, wherein the glycosylation site occurs at position 135 of SEQ ID NO:35.

114. The ATIII of claim 111, wherein the glycosylation site occurs at position 192 of SEQ ID NO:35.

115. The ATIII of claim 105, wherein the ATIII has enhanced heparin binding activity, and wherein the ATIII has a mutation at position 96, 135, 155, or 192 of SEQ ID NO:35.

116. An elastase-resistant antithrombin III (ATIII) comprising at least three modifications, wherein the modifications occur at positions P4, P5, and P6 of the ATIII, wherein P4, P5, and P6 are the fourth, fifth, and sixth amino acids towards the amino terminal side of the scissile bond of the reactive center respectively, wherein P4 comprises an amino acid selected from the group consisting of alanine; phenylalanine; glycine; and proline, wherein P5 comprises an amino acid selected from the group consisting of glutamic acid; phenylalanine; glycine; and proline, and wherein P6 comprises an amino acid selected from the group consisting of leucine, glycine, glutamic acid, and threonine, wherein the elastase-resistant ATIII has greater resistance to human neutrophil elastase as compared to plasma ATIII wherein the ATIII retains a factor Xa inhibitory activity which is at least about 12.5 percent of plasma ATIII factor Xa inhibitory activity.

117. The elastase-resistant ATIII of claim 116, wherein P6 is glycine.

118. The elastase-resistant ATIII of claim 117, wherein P5 is phenylalanine or glutamic acid.

119. An elastase-resistant antithrombin III (ATIII) comprising at least two modifications, wherein the modifications occur at positions P3 and P6 of the ATIII, wherein P3 and P6 are the third and sixth amino acids towards the amino terminal side of the scissile bond of the reactive center respectively, wherein P3 comprises an amino acid selected from the group consisting of isoleucine; serine; glycine; and asparagine, and wherein P6 comprises an amino acid selected from the group consisting of leucine; glycine; glutamic acid; and threonine, wherein the elastase-resistant ATIII has greater resistance to human neutrophil elastase as compared to plasma ATIII wherein the ATIII retains a factor Xa inhibitory activity which is at least about 12.5 percent of plasma ATIII factor Xa inhibitory activity.

120. The elastase-resistant ATIII of claim 119, wherein P3 is serine.

121. The elastase-resistant ATIII of claim 120, wherein P6 is glycine.

122. The elastase-resistant ATIII of claim 121, wherein P3 is serine.

123. An elastase-resistant antithrombin III (ATIII) comprising at least three modifications, wherein the modifications occur at positions P3, P6, and P7 of the ATIII, wherein P3, P6, and P7 are the third, sixth, and seventh amino acids towards the amino terminal side of the scissile bond of the reactive center respectively, wherein P3 comprises an amino acid selected from the group consisting of isoleucine; serine; glycine; and asparagine, wherein P6 comprises an amino acid selected from the group consisting of leucine; glycine; glutamic acid; and threonine, and wherein P7 comprises an amino acid selected from the group consisting of glutamic acid and glutamine, wherein the elastase-resistant ATIII has greater resistance to human neutrophil elastase as compared to plasma ATIII wherein the ATIII retains a factor Xa inhibitory activity which is at least about 12.5 percent of plasma ATIII factor Xa inhibitory activity.

124. The elastase-resistant ATIII of claim 123, wherein P7 is glutamic acid.

125. The elastase-resistant ATIII of claim 124, wherein P3 is serine, and wherein P6 is glycine.

126. An elastase-resistant antithrombin III (ATIII) comprising at least five amino acid modifications, wherein the modifications occur at positions P3, P4, P5, P6, and P7 of the ATIII, wherein P3, P4, P5, P6, and P7 are the third, fourth, fifth, sixth, and seventh amino acids towards the amino terminal side of the scissile bond of the reactive center respectively, wherein P3 is serine, wherein P4 is phenylalanine, wherein P5 is phenylalanine, wherein P6 is glycine, and wherein P7 is glutamic acid, wherein the resistant-resistant ATIII has greater resistance to human neutrophil lactase as compared to plasma ATIII wherein the ATIII retains a factor Xa inhibitory activity which is at least about 12.5 percent of plasma ATIII factor Xa inhibitory activity.

127. An elastase-resistant antithrombin III (ATIII) comprising at least five amino acid modifications, wherein the modifications occur at positions P3, P4, P5, P6, and P7 of the ATIII, wherein P3, P4, P5, P6, and P7 are the third, fourth, fifth, sixth, and seventh amino acids towards the amino terminal side of the scissile bond of the reactive center respectively, wherein P3 is serine, wherein P4 is alanine, wherein P5 is glutamic acid, wherein P6 is glycine, and wherein P7 is glutamic acid, wherein the elastase-resistant ATIII has greater resistance to human neutrophil elastase as compared to plasma ATIII wherein the ATIII retains a factor Xa inhibitory activity which is at least about 12.5 percent of plasma ATIII factor Xa inhibitory activity.

128. An elastase-resistant antithrombin III (ATIII) comprising at least two modifications, wherein the modifications occur at positions P4 and P5 of the ATIII, wherein P4 and P5 are the fourth and fifth amino acids towards the amino terminal side of the scissile bond of the reactive center respectively, wherein P4 comprises an amino acid selected from the group consisting of alanine; glycine; and proline, and wherein P5 comprises an amino acid selected from the group consisting of glutamic acid; glycine; and proline, wherein the elastase-resistant ATIII has greater resistance to human neutrophil elastase as compared to plasma ATIII wherein the ATIII retains a factor Xa inhibitory activity which is at least about 12.5 percent of plasma ATIII factor Xa inhibitory activity.

129. An elastase-resistant antithrombin III (ATIII) comprising at least three modifications, wherein the modifications occur at positions P4, P5, and P6 of the ATIII, wherein P4, P5, and P6 are the fourth, fifth, and sixth amino acids towards the amino terminal side of the scissile bond of the reactive center respectively, wherein P4 is alanine, wherein P5 is glutamic acid; and wherein P6 is leucine, wherein the elastase-resistant ATIII has greater resistance to human neutrophil elastase as compared to plasma ATIII wherein the ATIII retains a factor Xa inhibitory activity which is at least about 12.5 percent of plasma ATIII factor Xa inhibitory activity.

130. An elastase-resistant antithrombin III (ATIII) comprising at least four modifications, wherein the modifications occur at positions P3, P4, P5, and P6 of the ATIII, wherein P3, P4, P5, and P6 are the third, fourth, fifth, and sixth amino acids towards the amino terminal side of the scissile bond of the reactive center respectively, wherein P3 is isoleucine, wherein P4 is alanine, wherein P5 is glutamic acid; and wherein P6 is leucine, wherein the elastase-resistant ATIII has greater resistance to human neutrophil elastase as compared to plasma ATIII wherein the ATIII retains a factor Xa inhibitory activity which is at least about 12.5 percent of plasma ATIII factor Xa inhibitory activity.

131. An elastase-resistant antithrombin III (ATIII) comprising four modifications, wherein the modifications occur at positions P3, P4, P5, and P6 of the ATIII, wherein P3, P4, P5, and P6 are the third, fourth, fifth, and sixth amino acids towards the amino terminal side of the scissile bond of the reactive center respectively, wherein P3 is isoleucine, wherein P4 alanine, wherein P5 is glutamic acid; and wherein P6 is leucine, wherein the elastase-resistant ATIII has greater resistance to human neutrophil elastase as compared to plasma ATIII wherein the ATIII retains a factor Xa inhibitory activity which is at least about 12.5 percent of plasma ATIII factor Xa inhibitory activity.

132. An elastase-resistant antithrombin III (ATIII) comprising at least two modifications, wherein the modifications occur at positions P4 and P6 of the ATIII, wherein P4 and P6 are the fourth and sixth amino acids towards the amino terminal side of the scissile bond of the reactive center respectively, wherein P4 comprises an amino acid selected from the group consisting of alanine; phenylalanine; glycine; and proline, and wherein P6 comprises an amino acid selected from the group consisting of leucine; glycine; glutamic acid; and threonine, wherein the elastase-resistant ATIII has greater resistance to human neutrophil elastase as compared to plasma ATIII wherein the ATIII retains a factor Xa inhibitory activity which is at least about 12.5 percent of plasma ATIII factor Xa inhibitory activity.

133. The ATIII of claim 132, wherein the P4 is alanine and P6 is leucine.

134. The elastase-resistant ATIII of claim 133, wherein the ATIII has enhanced heparin binding activity, and wherein the ATIII has a mutation two residues subsequent to a glycosylation site.

135. The ATIII of claim 134, wherein the ATIII is in a pharmaceutically acceptable formulation.

136. The ATIII of claim 134, wherein the glycosylation site occurs at position 135 of SEQ ID NO:35.

137. The ATIII of claim 134, wherein the glycosylation site occurs at position 155 of SEQ ID NO:35.

138. The ATIII of claim 132, wherein the ATIII has enhanced heparin binding activity, and wherein the ATIII has a mutation at position 96, 135, 155, or 192 of SEQ ID NO:35.

* * * * *

UNITED STATES PATENT AND TRADEMARK OFFICE
CERTIFICATE OF CORRECTION

PATENT NO. : 6,878,813 B2
APPLICATION NO. : 10/014658
DATED : April 12, 2005
INVENTOR(S) : Bock et al.

It is certified that error appears in the above-identified patent and that said Letters Patent is hereby corrected as shown below:

On page 3, lines 8-9, replace "Grant Number HL-56914" with --Grant Numbers HL-56914, HL45486, and HL30712--

Signed and Sealed this

Thirteenth Day of March, 2007

JON W. DUDAS
*Director of the United States Patent and Trademark Office*